United States Patent
Buesseler et al.

(10) Patent No.: US 11,367,947 B2
(45) Date of Patent: *Jun. 21, 2022

(54) FIELD CONCENTRATING ANTENNAS FOR MAGNETIC POSITION SENSORS

(71) Applicant: St. Jude Medical International Holding S.à r.l., Luxembourg (LU)

(72) Inventors: Ryan Kenneth Buesseler, Delano, MN (US); Alexander Carson Houck, Hopkins, MN (US)

(73) Assignee: St. Jude Medical International Holding S.á r.l., Luxembourg (LU)

( * ) Notice: Subject to any disclaimer, the term of this patent is extended or adjusted under 35 U.S.C. 154(b) by 1600 days.

This patent is subject to a terminal disclaimer.

(21) Appl. No.: 15/072,185

(22) Filed: Mar. 16, 2016

(65) Prior Publication Data

US 2016/0276739 A1 Sep. 22, 2016

Related U.S. Application Data

(60) Provisional application No. 62/133,993, filed on Mar. 16, 2015.

(51) Int. Cl.
*A61B 5/00* (2006.01)
*A61B 5/06* (2006.01)
(Continued)

(52) U.S. Cl.
CPC .............. *H01Q 1/273* (2013.01); *A61B 5/06* (2013.01); *A61B 5/062* (2013.01);
(Continued)

(58) Field of Classification Search
CPC ...... A61B 2034/2051; A61B 2090/376; A61B 18/1492; A61B 2034/2072;
(Continued)

(56) References Cited

U.S. PATENT DOCUMENTS 5,513,637 A * 5/1996 Twiss ................ A61B 5/06
128/903
5,521,609 A * 5/1996 Desch ................ H01Q 7/08
343/787

(Continued)

FOREIGN PATENT DOCUMENTS

JP 2005057444 A 3/2005

OTHER PUBLICATIONS

Coillot, et al., "Induction Magnetometers Principle, Modeling and Ways of Improvement." Title of Publication: Magnetic Sensors—Principles and Applications. Publisher: InTech. Chapter 3. Published online Mar. 9, 2012 at https://www.intechopen.com/books/magnetic-sensors-principles-and-applications.

*Primary Examiner* — Baisakhi Roy
(74) *Attorney, Agent, or Firm* — Dykema Gossett PLLC

(57) ABSTRACT

A medical device is configured for diagnosis or treatment of a tissue within a body. The medical device comprises an elongate member and a position sensor. The elongate member is configured to be received within the body, and has a lumen extending between a proximal end and a distal end. The position sensor is disposed within the lumen proximate the distal end of the deformable member. The position sensor comprises a coil wound to form a central passage and configured to generate a current flow when subject to a magnetic field, and a high-permeability antenna having at least a portion disposed outside the central passage to concentrate the magnetic field into the coil and increase the current flow.

34 Claims, 18 Drawing Sheets

(51) Int. Cl.
*H01Q 1/27* (2006.01)
*H01Q 7/06* (2006.01)
*A61B 34/20* (2016.01)
*A61B 18/14* (2006.01)
*A61B 90/00* (2016.01)

(52) U.S. Cl.
CPC .......... *A61B 18/1492* (2013.01); *A61B 34/20* (2016.02); *H01Q 7/06* (2013.01); *A61B 2034/2051* (2016.02); *A61B 2034/2072* (2016.02); *A61B 2090/376* (2016.02)

(58) Field of Classification Search
CPC ... A61B 2562/0223; A61B 34/20; A61B 5/06; A61B 5/062
See application file for complete search history.

(56) References Cited

U.S. PATENT DOCUMENTS

| | | |
|---|---|---|
| 6,233,476 B1 | 5/2001 | Strommer et al. |
| 6,332,089 B1 * | 12/2001 | Acker ................. A61B 5/0422 128/899 |
| 6,590,536 B1 * | 7/2003 | Walton ............... A63B 71/0622 342/463 |
| 7,197,354 B2 | 3/2007 | Sobe |
| 7,386,339 B2 | 6/2008 | Strommer et al. |
| 8,979,837 B2 | 3/2015 | de la Rama et al. |
| 9,220,461 B2 | 12/2015 | Samuelsson et al. |
| 10,898,104 B2 * | 1/2021 | Olson .................. A61B 5/6852 |
| 2002/0032380 A1 * | 3/2002 | Acker ................. A61B 1/00059 600/439 |
| 2004/0021463 A1 * | 2/2004 | Miyazawa ......... G01R 29/0878 324/252 |
| 2004/0220461 A1 * | 11/2004 | Schwartz ............. A61B 5/0422 600/374 |
| 2008/0183071 A1 | 7/2008 | Strommer et al. |
| 2011/0066029 A1 | 3/2011 | Lyu et al. |
| 2011/0130750 A1 | 6/2011 | Ormsby et al. |
| 2011/0301497 A1 * | 12/2011 | Shachar ................ A61B 1/041 600/567 |
| 2011/0313417 A1 | 12/2011 | de la Rama et al. |
| 2012/0158080 A1 * | 6/2012 | Connelly ............. A61N 1/3718 607/9 |
| 2012/0172761 A1 | 7/2012 | Meller et al. |
| 2014/0200556 A1 | 7/2014 | Sela et al. |
| 2016/0022958 A1 * | 1/2016 | Sobe .................. A61B 17/3207 600/424 |

* cited by examiner

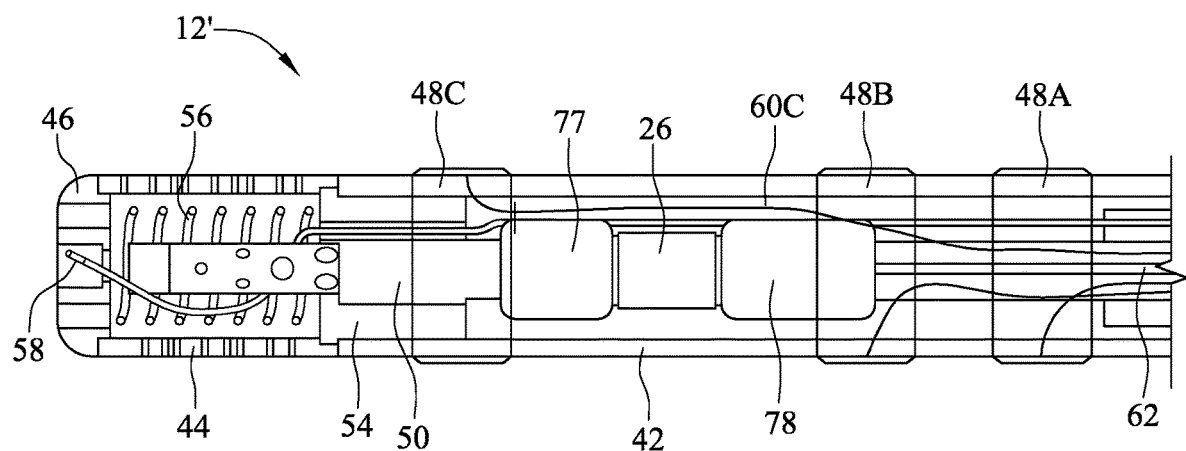
FIG. 5
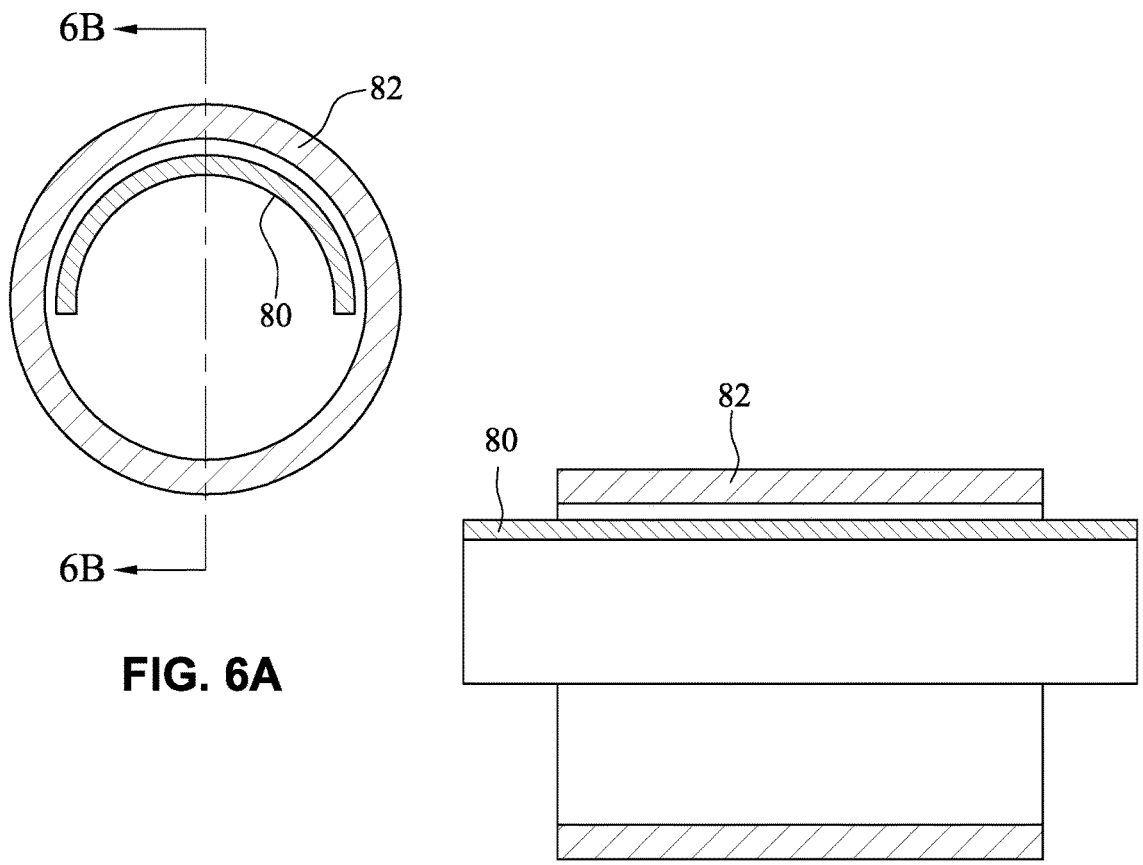
FIG. 6A
FIG. 6B

FIELD CONCENTRATING ANTENNAS FOR MAGNETIC POSITION SENSORS

CROSS-REFERENCE TO RELATED APPLICATIONS

This application claims the benefit of U.S. provisional application No. 62/133,993, 16 Mar. 2015, which is hereby incorporated by reference as though fully set forth herein.

BACKGROUND a. Field

The instant disclosure relates to magnetic sensors, such as those used in medical positioning systems. In one embodiment, the instant disclosure relates to antennas for increasing the signal strength of magnetic sensors.

b. Background Art

Medical positioning systems have the capability of tracking a medical device within a known three-dimensional tracking space. Typical medical devices used with medical positioning systems include catheters, introducers, guide wires and the like. Each of these medical devices may use elongate, flexible shafts on which various operational elements, such as electrodes, are used to perform various diagnosis or treatment procedures, such as mapping and ablation, on anatomy, such as the heart.

Some types of medical positioning systems utilize a plurality of magnetic fields to induce voltage in a position sensor having one or more coils in order to determine the location of that sensor within a three-dimensional space defined by the magnetic fields. The voltage induced in such sensors can be measured by an electronic control unit as a signal indicative of the location of the sensor. The reliability and accuracy of the magnetic positioning system is related to the dependability of the sensor signal. As such, it is beneficial to increase the strength of the voltage induced in the coil.

One method of increasing the output strength of the sensor is to position a high permeability core within the coil winding to increase the electric voltage generated by the coil. The presence of the core increases the magnetic flux density by drawing magnetic field lines toward the sensor. Once such sensor coil and core combination is described in U.S. Pat. No. 7,197,354 to Sobe, entitled "System for Determining the Position and Orientation of a Catheter."

The effectiveness of prior art cores is limited by the geometry of the sensor and the medical device into which it is installed. For a medical device having an elongate, flexible shaft, it is desirable that the device have a small diameter, e.g., less than 19 French (approximately 6.33 millimeters), so as to enable movement through the vasculature. Sensors used within typical medical devices can be even smaller, on the order of 1 French (0.33 millimeters) or less. As such, the spaces available for the position sensor within the medical device and the core within the sensor are small.

The foregoing discussion is intended only to illustrate the present field and should not be taken as a disavowal of claim scope.

BRIEF SUMMARY

The instant disclosure relates to position sensors used in medical devices for use with medical positioning systems. Such medical devices may comprise mapping and ablation catheters for diagnosing and treating cardiac arrhythmias via, for example, radio frequency (RF) ablation. In particular, the instant disclosure relates to antennas, concentrators, levers, or similar structures for inducing magnetic flux flow within a position sensor and thereby increasing the signals generated by the position sensor.

In one embodiment, a medical device is configured for diagnosis or treatment of a tissue within a body. The medical device comprises an elongate, deformable member and a position sensor. The elongate member is configured to be received within the body, and has a lumen extending between a proximal end and a distal end. The position sensor is disposed within the lumen proximate the distal end of the deformable member. The position sensor comprises a coil wound to form a central passage and configured to generate a voltage when subject to a magnetic field, and a high-permeability antenna having at least a portion disposed outside the central passage so as to concentrate the magnetic field into the coil and increase the resulting voltage.

In another embodiment, a position sensor assembly for a medical device comprises a body defining an internal lumen, a wire winding supported by the body, and a magnetic flux antenna disposed outside of the wire winding and within the body.

In yet another embodiment, a medical device comprises an elongate sheath defining a lumen, a position sensor disposed within the lumen, an electrode exposed to an exterior of the elongate sheath, and a magnetic antenna disposed within the sheath apart from the position sensor.

In still another embodiment, a method of increasing the signal output of a magnetic position sensor comprises configuring a magnetic position sensor comprising a coil to generate a voltage when subject to a magnetic field, mounting the position sensor within a medical device, and placing at least a portion of a high permeability antenna outside of the magnetic position sensor so as to be configured to concentrate a magnetic field into the coil and increase the current flow.

The foregoing and other aspects, features, details, utilities, and advantages of the present disclosure will be apparent from reading the following description and claims, and from reviewing the accompanying drawings.

BRIEF DESCRIPTION OF THE DRAWINGS

FIG. 5 is a partial cross-sectional view of a distal portion of a medical device showing the location of two field concentrating antennas relative to a magnetic position sensor.

FIGS. 6A and 6B are radial and axial cross-sectional views, respectively, of a second embodiment of a field concentrating antenna and for a magnetic position sensor in which the antenna comprises an arcuate thin film extending through the position sensor.

DETAILED DESCRIPTION OF EMBODIMENTS

Several embodiments of field concentrating antennas for magnetic position sensors are disclosed herein. In general, these field concentrating antennas are used in medical devices to increase the output signal of position sensors used in conjunction with medical positioning systems, particularly magnetic positioning systems. In one embodiment, the antennas help produce high gain induction sensors that can be used within medical devices used in conjunction with magnetic medical positioning systems. Details of the various embodiments of the present disclosure are described below with specific reference to the figures.

Figure 1:
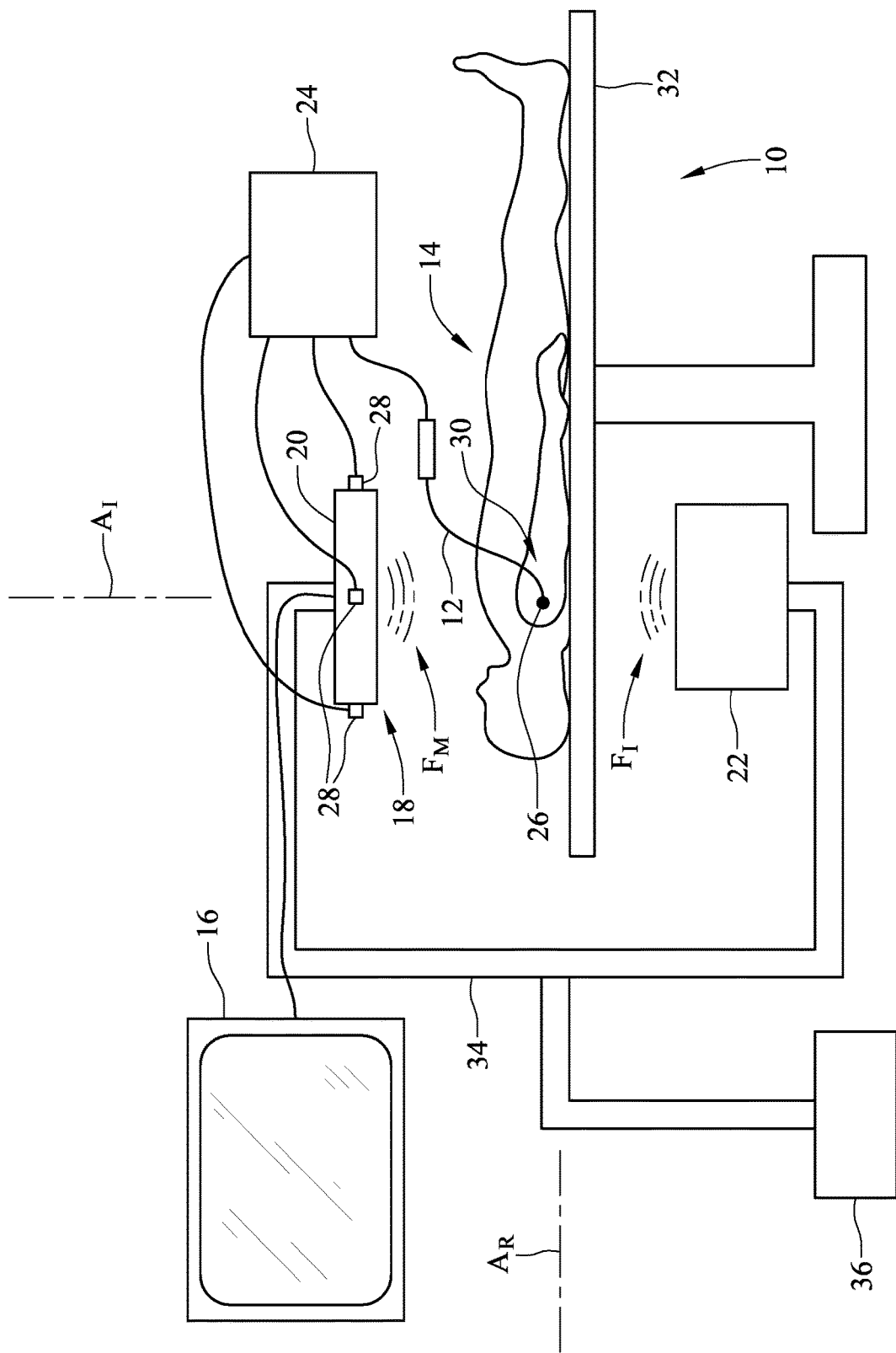
FIG. 1 is a schematic representation of a medical imaging system for generating and displaying data on a display screen using a medical device having a position sensor.

FIG. 1 is a schematic representation of medical imaging system 10 for determining the position of catheter 12 relative to a model of an organ of patient 14, as well as for generating and displaying the model and related information on display unit 16. System 10 includes moving imager 18, which includes intensifier 20 and emitter 22, and magnetic positioning system (MPS) 24, which includes position sensor 26 and field generators 28. Electrophysiology map information and cardiac mechanical activation data pertaining to the model generated by medical imaging system 10 is displayed on computer display 16 to facilitate diagnosis and treatment of patient 14. The present disclosure describes a way to increase the signal output of a position sensor located within catheter 12 so that system 10 is better able to process data collected by catheter 12. For example, catheter 12 may include a coil in which a voltage is induced by the presence of a magnetic field generated by MPS 24. The ability of the coil to interact with the magnetic field, and thereby generate current, is increased with the use of the field concentrating antennas of the present disclosure.

Moving imager 18 is a device which acquires an image of region of interest 30 while patient 14 lies on operation table 32. Intensifier 20 and emitter 22 are mounted on C-arm 34, which is positioned using moving mechanism 36. In one embodiment, moving imager 18 comprises a fluoroscopic or X-ray type imaging system that generates a two-dimensional (2D) image of the heart of patient 14.

MPS 24 includes a plurality of magnetic field generators 28 and catheter 12, to which position sensor 26 is mounted at a distal end and handle 38 is connected at a proximal end. MPS 24 determines the position of the distal portion of catheter 12 in a magnetic coordinate system generated by field generators 28, according to output of position sensor 26. In one embodiment, MPS 24 comprises a MediGuide gMPS magnetic positioning system, as is commercially offered by St. Jude Medical, Inc., that simultaneously generates a three-dimensional (3D) model of the heart of patient 14.

C-arm 34 positions intensifier 20 above patient 14 and emitter 22 underneath operation table 32. Emitter 22 generates, and intensifier 20 receives, an imaging field $F_I$, e.g., a radiation field, that generates a 2D image of area of interest 30 on display 16. Intensifier 20 and emitter 22 of moving imager 18 are connected by C-arm 34 so as to be disposed at opposites sides of patient 14 along imaging axis $A_I$, which extends vertically with reference to FIG. 1 in the described embodiment. Moving mechanism 36 rotates C-arm 34 about rotation axis $A_R$, which extends horizontally with reference to FIG. 1 in the described embodiment. Moving mechanism 36 or an additional moving mechanism may be used to move C-arm 34 into other orientations. For example, C-arm 34 can be rotated about an axis (not shown) extending into the plane of FIG. 1 such that imaging axis $A_I$ is rotatable in the plane of FIG. 1. As such, moving imager 18 is associated with 3D optical coordinate system having x-axis $X_I$, y-axis $Y_I$, and z-axis $Z_I$.

MPS 24 is positioned to allow catheter 12 and field generators 28 to interact with system 10 through the use of appropriate wired and/or wireless technology. Catheter 12 is inserted into the vasculature of patient 14 such that position sensor 26 is located at area of interest 30. Field generators 28 are mounted to intensifier 20 so as to be capable of generating magnetic field $F_M$ in area of interest 30 coextensive with imaging field $F_I$. MPS 24 is able to detect the presence of position sensor 26 within the magnetic field $F_M$. In one embodiment, position sensor 26 may include three mutually orthogonal coils, as described in U.S. Pat. No. 6,233,476 to Strommer et al., the entire content of which is incorporated herein by reference in its entirety for all purposes. As such, MPS 24 is associated with a 3D magnetic coordinate system having x-axis $X_P$, y-axis $Y_P$, and z-axis $Z_P$.

The 3D optical coordinate system and the 3D magnetic coordinate system are independent of each other, that is they have different scales, origins, and orientations. Movement of C-arm 34 via moving mechanism 36 allows imaging field $F_I$ and magnetic field $F_M$ to move relative to area of interest 30 within their respective coordinate system. However, field generators 28 are located on intensifier 20 so as to register the coordinate systems associated with moving imager 18 and MPS 24. Thus, images generated within each coordinate system can be merged into a single image shown on display unit 16. Moving imager 18 and MPS 24 may function together as is described in United States Pub. No. US 2008/0183071 to Strommer et al., the entire content of which is incorporated herein by reference in its entirety for all purposes.

Display unit 16 is coupled with intensifier 20. Emitter 22 transmits radiation that passes through patient 14. The radiation is detected by intensifier 20 as a representation of the anatomy of area of interest 30. An image representing area of interest 30 is generated on display unit 16, including an image of catheter 12. C-arm 34 can be moved to obtain multiple 2D images of area of interest 30, each of which can be shown as a 2D image on display unit 16.

Display unit 16 is coupled to MPS 24. Field generators 28 transmit magnetic fields that are mutually orthogonal, corresponding to axes of the 3D magnetic coordinate system. Position sensor 26 detects the magnetic fields generated by field generators 28. The detected signals are related to the position and orientation of the distal end of catheter 12 by, for example, the Biot Savart law, known in the art. Thus, the precise position and location of the distal end of catheter 12 is obtained by MPS 24 and can be shown in conjunction with the 2D images of area of interest 30 at display unit 16. Furthermore, data from position sensor 26 can be used to generate a 3D model of area of interest 30, as is described in U.S. Pat. No. 7,386,339 to Strommer et al., the entire content of which is incorporated herein by reference in its entirety for all purposes.

The voltage output of position sensor 26 is increased by placement of a high magnetic permeable material adjacent to, in close proximity to, underneath, next to, or otherwise disposed in relation to the coil windings forming the sensor to increase magnetic field interaction with the position sensor. Increased voltage output of the position sensor increases the signal generated by the position sensor that is interpreted by MPS 24 and system 10. Improved signal strength can improve the accuracy of the placement of catheter 12 (i.e., position sensor 26) relative to the anatomy generated by emitter 22 and intensifier 20 on display screen 16, such as by increasing the signal-to-noise ratio of MPS 24. Furthermore, hardware used within system 10 may be able to use larger amplification levels and magnetic transmission frequencies. This is beneficial as it lowers the environmental influence to magnetic transmitters, which drives down positional error. Improved signal strength also permits smaller form factors for the design of the sensor, while maintaining the same signal output.

Figure 2:
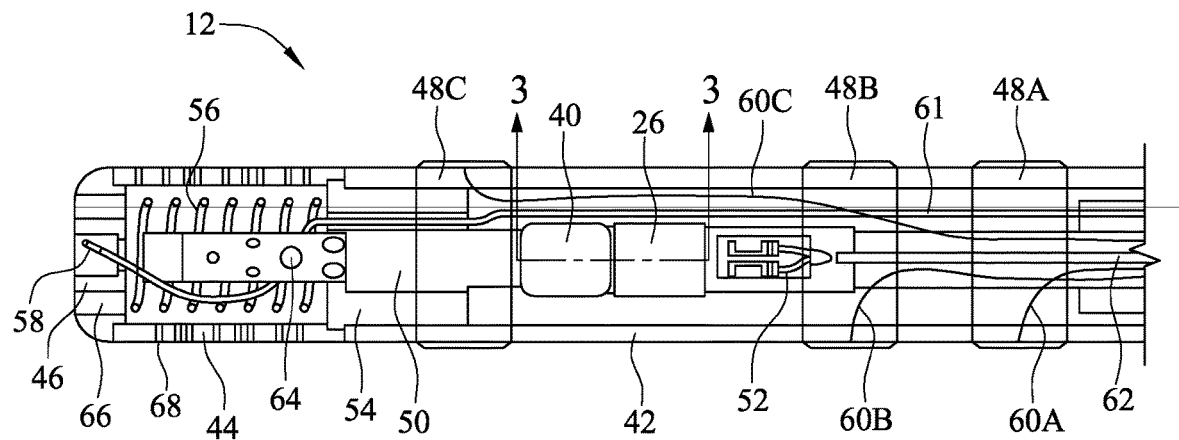
FIG. 2 is a partial cross-sectional view of a distal portion of the medical device of FIG. 1 showing one embodiment of a field concentrating antenna for a magnetic position sensor in which the antenna is located adjacent the position sensor.

FIG. 2 is a partial cross-sectional view of the distal portion of ablation catheter 12 of FIG. 1 showing position sensor 26 and field concentrating antenna 40. Catheter 12 also includes sheath 42, flexible tip 44, tip cap 46, electrodes 48A, 48B and 48C, fluid tube 50, flex circuit 52, plug 54, spring coil 56, and thermocouple 58.

Tube 50 is disposed concentrically within sheath 42 and is attached therein by an adhesive or the like. Tube 50 may be a PEEK tube or it may be made of other suitable nonconductive materials. Plug 54 is positioned around tube 50 to maintain tube 50 centered within sheath 42 and to facilitate joining of flexible tip 44 to sheath 42. For example, flexible tip 44 may be metallurgically joined to plug 54 at a flange. Flexible tip 44 includes incisions that allow flexible tip 44 to bend. Spring coil 56 is supported between tip cap 46 and plug 54 surrounding tube 50 and provides structural integrity to sheath 42 and resiliently maintains flexible tip 44 in a predetermined configuration when at rest and no force is placed on flexible tip 44. In the embodiment shown, the predetermined rest configuration orients the longitudinal axis of flexible tip 44 to follow a straight line coincident with a central axis of catheter 12.

Band electrodes 48A and 48B are provided on sheath 42 and may be used for diagnostic purposes or the like. Band electrode 48C is provided on sheath 42 and may be used for ablating tissue. Conductor wires 60A, 60B and 60C are provided to connect electrodes 48A, 48B and 48C, respectively, to the proximal portion of catheter 12, such as handle 38, for ultimate connection with MPS 24 and system 10. Thermocouple 58 is disposed in tip cap 46 and may be supported by an adhesive. Conductor wire 61 connects thermocouple 58 to the proximal portion of catheter 12, such as handle 38.

Position sensor 26 circumscribes tube 50 within sheath 42. Position sensor 26 is coupled to flex circuit 52, which includes conductor 62 to connect to the proximal portion of catheter 12, such as handle 38. In one embodiment, position sensor 26 comprises a wound conductor coil that is receptive to magnetic fields. Antenna 40 is positioned in close proximity to position sensor 26 in order to facilitate a higher amount of magnetic flux interacting with position sensor 26 (as opposed to configurations without antenna 40).

In operation, catheter 12 is inserted into the vasculature of a patient such that flexible tip 44 is located at an area where it is desirable to perform a medical procedure (e.g., near tissue that is to be ablated). Ablation energy (e.g., RF energy) could then be delivered through tip cap 46, flexible tip 44, and/or one or more of band electrodes 48A, 48B, and 48C. Flexible tip 44 is able to bend so as to allow, for example, band electrode 48C to contact the tissue with a reduced risk of puncturing or otherwise damaging the tissue. As mentioned, band electrodes 48A, 48B, and 48C may be used to gather physiological data from the patient.

Tube 50 allows an irrigation fluid to be conveyed to the ablation site in order to control the temperature of the tissue and remove impurities from the site. For example, irrigation fluid from an external storage tank may be connected to handle 38 whereby the fluid is introduced, e.g. pumped, into tube 50. Tube 50 is provided with (or is affixed to a distal component that is provided with) radial ports 64 to allow fluid to escape tube 50. Fluid is permitted to escape catheter 12 at tip ports 66 in tip cap 46 and ports 68 in flexible tip 44 formed by the noted incisions. Thermocouple 58 permits operators of system 10 to monitor the temperature of or near the ablation site.

Position sensor 26 allows for accurate placement of, for example, band electrode 48C within the patient. Antenna 40 increases the signal generated by position sensor 26 to increase the accuracy of the location data. As discussed below, antenna 40 comprises a mass of high permeability material that is placed in close proximity to position sensor 26 to funnel or concentrate magnetic flux into position sensor 26 to increase the current generated within the coil winding of position sensor 26. Additional details of the construction of sheath 42, flexible tip 44, fluid tube 50, spring coil 56, and other components of catheter 12 can be found in, for example, United States Pub. No. US 2010/0152731, now U.S. Pat. No. 8,979,837, and United States Pub. No. US 2011/0313417, both to de la Rama et al., the entire contents of which are incorporated herein by reference in their entirety for all purposes. Additional details of the construction of position sensor 26, flex circuit 52, and other components can be found in United States Pub. No. US 2014/0200556 to Sela et al., the entire content of which is incorporated herein by reference in its entirety for all purposes.

Figure 3:
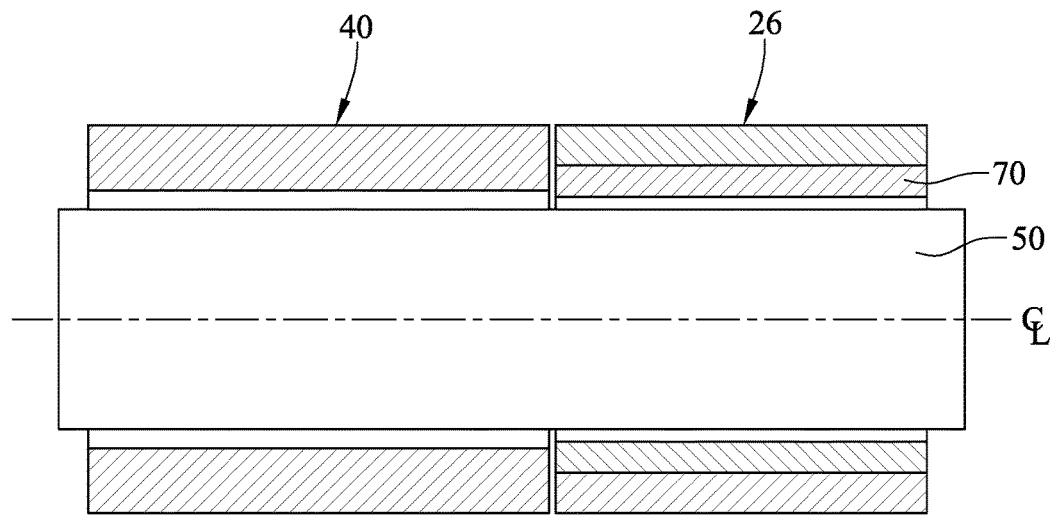
FIG. 3 is a cross-sectional view of the magnetic position sensor and field concentrating antenna of FIG. 2 showing the presence of a conventional core within a central passage of the position sensor.

FIG. 3 is a cross-sectional view of magnetic position sensor 26 and field concentrating antenna 40 of FIG. 2. FIG. 3 schematically depicts fluid tube 50 disposed concentrically along the axis of center line CL, with position sensor 26 and antenna 40 positioned to circumscribe tube 50. Although, as shown in the other Figures, sensor 26 and antenna 40 need not be axially aligned with center line $C_L$. In the embodiment shown, position sensor 26 comprises a coil winding (see coil windings 74 of FIG. 4) having an internal, central passage in which core 70 is disposed and through which tube 50 extends. The coil windings 74 of position sensor 26 may be formed from a length of conductive wire, such as copper, spirally wound about center line $C_L$. In one embodiment, the ends of the wire (see wires 76A, 76B of FIG. 4) extend toward the proximal portion of catheter 12 to join to flexible circuit 52 (FIG. 2). In addition to the wire routing depicted in FIG. 4, the wiring of position sensor 26 may extend from different locations on position sensor 26 and may be routed to extend to other locations of catheter 12. The coil windings may be supported by a bobbin or other support structure (see, e.g., structure 72 of FIG. 4). In other embodiments, the coil winding may be embedded within sheath 42.

Continuing to refer to FIG. 3, in the depicted embodiment, position sensor 26 includes core 70, which can be used to increase the magnetic flux passing through the coil windings of position sensor 26. Core 70 comprises a conventional annular core constructed of high permeability material, such as those described in the aforementioned U.S. Pat. No. 7,197,354 to Sobe, the entire content of which is incorporated herein by reference in its entirety for all purposes. In the depicted embodiment, core 70 does not extend beyond the outer axial limits of position sensor 26, which may be useful in winding of the wires around core 70 during manufacturing. In other embodiments, core 70 may extend beyond the outer axial limits of position sensor 26. As such, the inner diameter of the coil windings 74 comprising part of position sensor 26 needs to be sufficiently large to accommodate the use of core 70. However, in other embodiments, core 70 may have a larger diameter than position sensor 26. In yet other embodiments, position sensor 26 does not include core 70.

Antenna 40 comprises an annular body having an internal, central passage through which tube 50 extends. Antenna 40 is positioned adjacent position sensor 26 and may be either in contact with position sensor 26 or spaced from position sensor 26 a short distance (e.g., the width of position sensor 26) without the use of a remote tether (see, for example, conductor 102 in FIG. 9). Antenna 40 is configured to generate magnetic flux lines that pass through position sensor 26 when subject to a magnetic field, thereby bringing a larger amount of the magnetic field into contact with position sensor 26 than would otherwise contact position sensor 26 without the presence of antenna 40.

Figure 4:
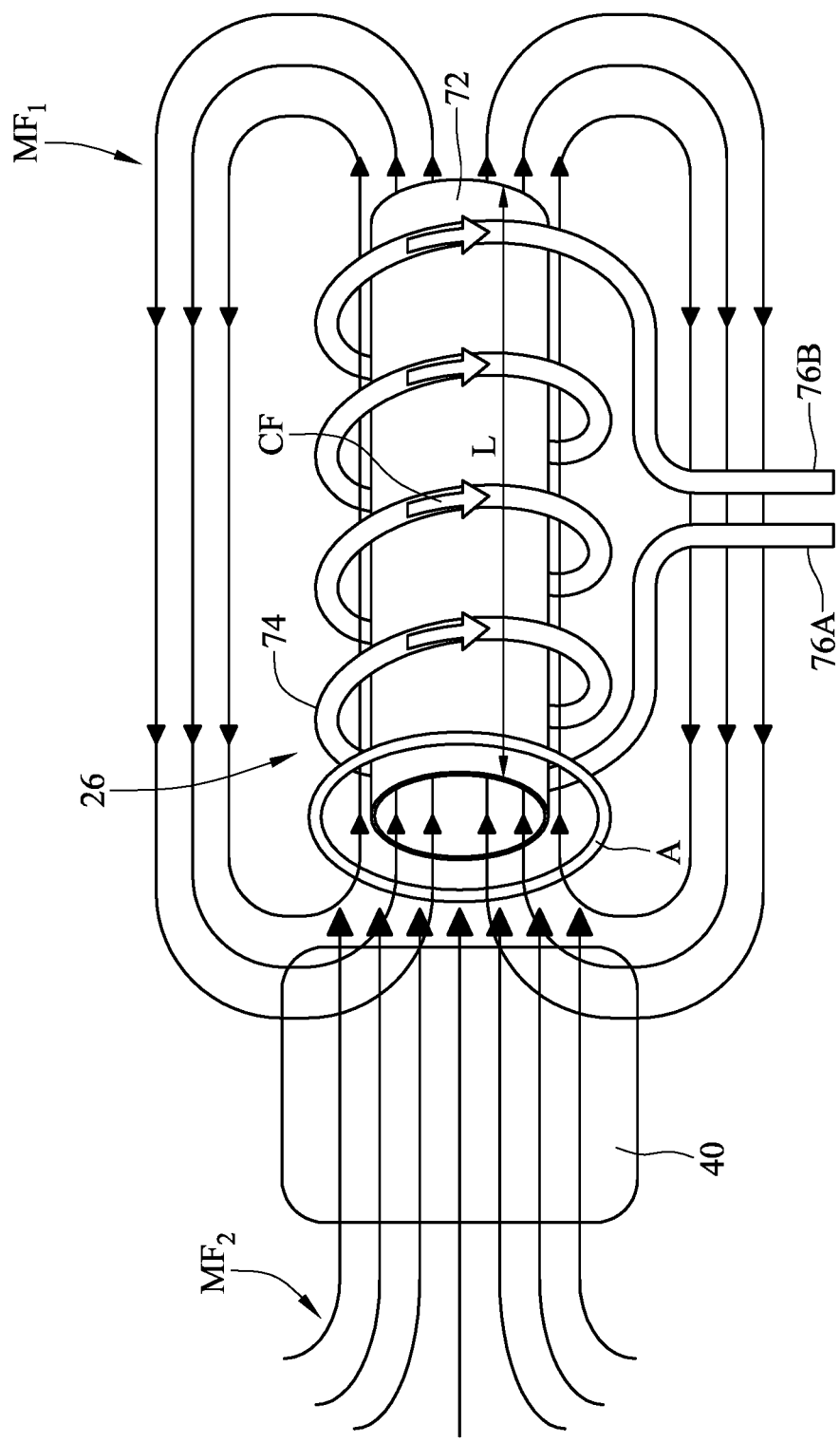
FIG. 4 is a schematic diagram of the magnetic position sensor and the field concentrating antenna of FIG. 3 illustrating the presence of magnetic flux lines and induced current flow.

FIG. 4 is a schematic diagram of magnetic position sensor 26 and field concentrating antenna 40 of FIG. 3 illustrating the presence of magnetic flux lines $MF_1$ and $MF_2$, and induced current flow CF. Position sensor 26 may include structure 72, such as core 70 or a bobbin, around which coil windings 74 are wound in a spiral fashion between lead wires 76A and 76B. Lead wires 76A and 76B extend from coil windings 74 to join to flex circuit 52 (FIG. 2). As a result of being placed in a magnetic field, such as magnetic field $F_M$ of FIG. 1, magnetic flux lines $MF_1$ are formed by coil windings 74, which induces current flow CF in coil windings 74. The voltage V induced in coil windings 74 between lead wires 76A and 76B is defined in Equation (1) below, where =magnetic permeability (core material), N=total number of turns, A=cross-sectional area of core (L=length of core), and B=magnetic field strength (output of drive coil, in P-P or RMS).

$$V = 2\pi \mu NABf \qquad \text{Equation (1)}$$

As can be seen from Equation (1), the induced voltage V is increased if the magnetic permeability μ increases or if the area A increases. It is, however, undesirable to increase the area A of the core due to space limitations within catheter 12, as well as the overall outer diameter size limitations of catheter 12. It is also not always possible to simply increase the number of turns N of the coil without unduly affecting the flexibility of the catheter. For example, adding windings in the axial length makes the sensor longer, while adding winding in the radial direction makes the sensor thicker, both of which may make the catheter undesirably stiffer.

As a result of being subject to the same magnetic field that position sensor 26 is subject to, magnetic flux lines $MF_2$ are formed by antenna 40. Some of magnetic flux lines $MF_2$ pass through position sensor 26. With reference to Equation (1), antenna 40 can be viewed as either increasing the permeability μ of the core, or as increasing the magnetic field strength B impacting the core. As a result of the presence of antenna 40, various design parameters of position sensor 26, such as voltage V or area A, can be changed. For example, the size (e.g., diameter D, wherein $$A = \pi \left(\frac{D}{2}\right)^2$$

of coil windings 74 could be reduced without reducing the signal strength or V by using an appropriately sized antenna 40. Additionally, antenna 40 may also permit the windings of position sensor 26 to be fabricated from cheaper materials or based on connection methods to flex circuit 52 (visible in FIG. 2), for example, while allowing for the specific configuration of antenna 40 to generate the desired signal strength. Also, antenna 40 can merely be configured as a mass of high permeability material that is used to simply increase voltage V, which increases the signal of position sensor 26 received at MPS 24 (shown in FIG. 1). Voltage V could be further increased by including multiple antennas within catheter 12.

FIG. 5 is a partial cross-sectional view of a distal portion of ablation catheter 12' showing the location of field concentrating antenna 77 and field concentrating antenna 78 relative to magnetic position sensor 26. In the depicted embodiment, antenna 78 is disposed adjacent position sensor 26 axially opposite antenna 77. In other embodiments, antennas 77 and 78 can be positioned on the same side of position sensor 26. Antennas 77 and 78 can be in contact with, adjacent to, or spaced from position sensor 26. Antennas 77 and 78 can be configured similarly as antenna 40 as is described with reference to FIGS. 2-4. For example, antennas 77 and 78 may each simply comprise a cylindrical body positioned in close proximity to coil windings 74 (visible in FIG. 4). However, in the depicted embodiment of FIG. 5, antennas 40 and 78 have outer diameters larger than that of position sensor 26 thereby distinguishing from conventional cores that must be smaller for placement within the position sensor. The cylindrical shape allows for other components of catheter 12', such as tube 50, flex circuit 52 (visible in FIG. 2) or lead wires, to pass therethrough.

The antennas described herein can be made of any material, with materials of higher magnetic permeability being more suitable. Magnetic field lines preferentially travel through materials with high permeability. In various embodiments, Mu metals, amorphous metal alloys (also known as metallic glass alloys), or 99.95% pure iron may be used. One particular branch of Mu metals and Metglas® amorphous alloys (METGLAS is a registered trademark of Metglas, Inc. of Conway, S.C.) are both particularly well suited for use with antennas of the present disclosure. As used herein, the term "Metglas" means thin amorphous metal alloys (also known as metallic glass alloys) produced using a rapid solidification process (e.g., cooling at about one million degrees Fahrenheit per second), whether or not bearing the METGLAS trademark and whether or not produced by Metglas, Inc. or one of its related entities. That said, Metglas alloy 2714A has been found to work well in certain applications/constructions. The Metglas components used in the antennas disclosed herein are thin ribbons/sheets of various widths that are generally 15-75 microns (i.e., 0.015-0.075 mm) thick, but thinner or thicker ribbons/sheets could be used. The Metglas strips discussed herein may be, for example, anywhere from approximately 0.020" to 0.100" wide. Further, as compared to air with a magnetic permeability equal to one (i.e., μ=1), it has been found that Mu metals have a relative magnetic permeability of approximately 50,000, 99.95% pure iron has a relative magnetic permeability of approximately 200,000, and Metglas has a relative magnetic permeability of approximately 1,000,000.

"Magnetic permeability" as used herein, unless indicated to the contrary, refers to the ability of a material or element to support the formation of a magnetic field within itself. It is the degree of magnetization that a material obtains in response to an applied magnetic field. A material with a "high magnetic permeability" as used herein, unless indicated to the contrary, means any material having a relative magnetic permeability above the relative magnetic permeability of Martensitic stainless steel.

The specific shape of antennas 40, 77, and 78 can be varied to achieve desirable design requirements. For round antenna shapes having a diameter D and a length L, experiments have shown that the shape of high permeability antennas is optimized when the D/L ratio is small. Antennas having such shape are typically long and skinny.

FIGS. 6A and 6B are radial and axial cross-sectional views, respectively, of field concentrating antenna 80 and magnetic position sensor 82. Position sensor 82 is similar to position sensor 26 discussed with reference to FIGS. 2 and 3, but without a core. Antenna 80 comprises an arcuate thin film, sheet, or ribbon extending axially through position sensor 82. As compared to a conventional sensor core, mass of antenna 80 is displaced from the interior of position sensor 82 and located outside of the boundaries of position sensor 82. Clearing antenna 80 from interior portions of position sensor 82 allows for position sensor 82 to be smaller without sacrificing signal strength, or for placement of other components within the sensor, which increase the design flexibility of the medical device.

In one embodiment, antenna 80 is thin in that the radial thickness of antenna 80 is orders of magnitude smaller that the circumferential width or axial length of antenna 80. For example, the radial thickness of antenna 80 may be approximately fifteen microns (i.e., 15 μm, which is 0.015 mm) or less. In the depicted embodiment, the axial length of antenna 80 is longer than the axial length of position sensor 82 so that antenna 80 necessarily extends from position sensor 82 when arranges as shown in FIGS. 6A and 6B. However, in other embodiments, antenna 80 may be equally long or shorter than position sensor 82, but positioned so as to extend axially out from position sensor 82 (e.g., see the configuration shown in FIGS. 7A and 7B, where the antenna 84 is the same length as the magnetic position sensor 86). In the embodiment shown in FIGS. 6A and 6B, antenna 80 comprises half of a hollow cylindrical shell (i.e., is a semi-cylindrical shell or a half cylinder), although other sub-cylindrical (i.e., having less than a full circular cross section) or arcuate shapes may be used. Also, the antenna may be flat (i.e., have a square or rectangular cross section rather than an arcuate cross section), as shown in FIGS. 7A and 7B.

Figure 7A:
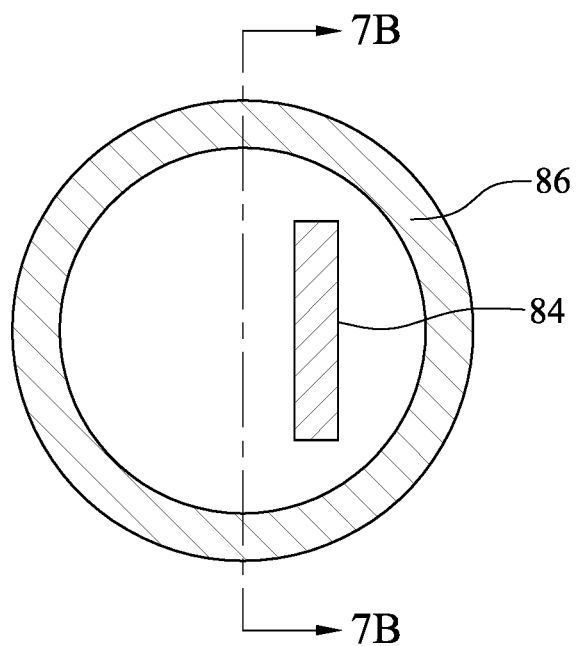
FIGS. 7A and 7B are radial and axial cross-sectional views, respectively, of a third embodiment of a field concentrating antenna and for a magnetic position sensor in which the antenna comprises an elongated thin film extending from the position sensor.
Figure 7B:
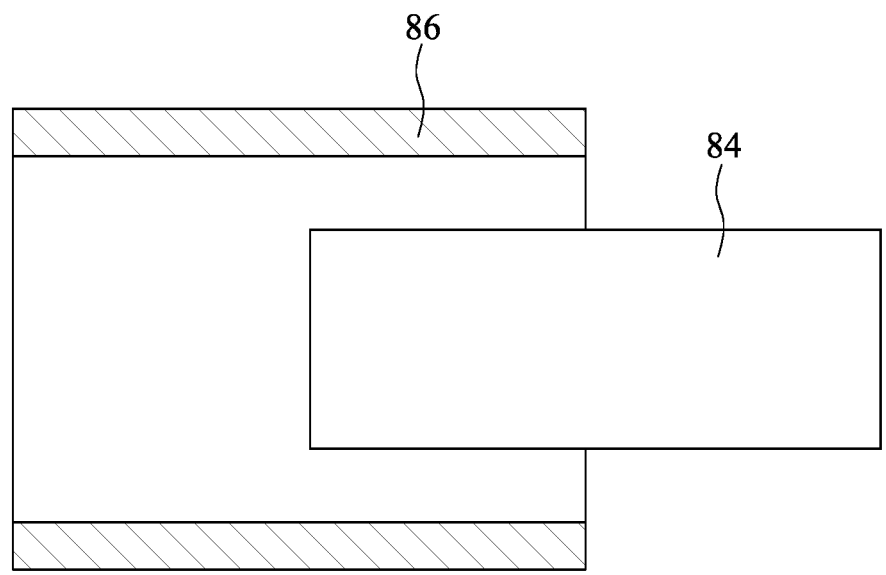

FIGS. 7A and 7B are radial and axial cross-sectional views, respectively, of field concentrating antenna 84 and magnetic position sensor 86. Antenna 84 comprises a flat thin film extending axially from position sensor 86. Antenna 84 is similar to that of antenna 80 of FIGS. 6A and 6B, but antenna 84 is flat and axially equal in length to position sensor 86. Antenna 84 is positioned partially within and partially outside of position sensor 86. Antenna 84 may also be placed completely outside of position sensor either distally or proximally of position sensor 86. Antenna 84 depicts another embodiment of a field concentrating antenna of the present disclosure in which the antenna can be displaced at least partially from the interior of the position sensor 86 (e.g., at least a portion of the antenna 84 extending from the interior of the sensor 86) in order to increase design options for the overall diameter of position sensor 86 or the contents of the interior of position sensor 86. In other embodiments, a thin film antenna may be configured to extend along a majority of the length of the elongate, flexible member used in the medical device, including along any distal loop regions.

Figure 8A:
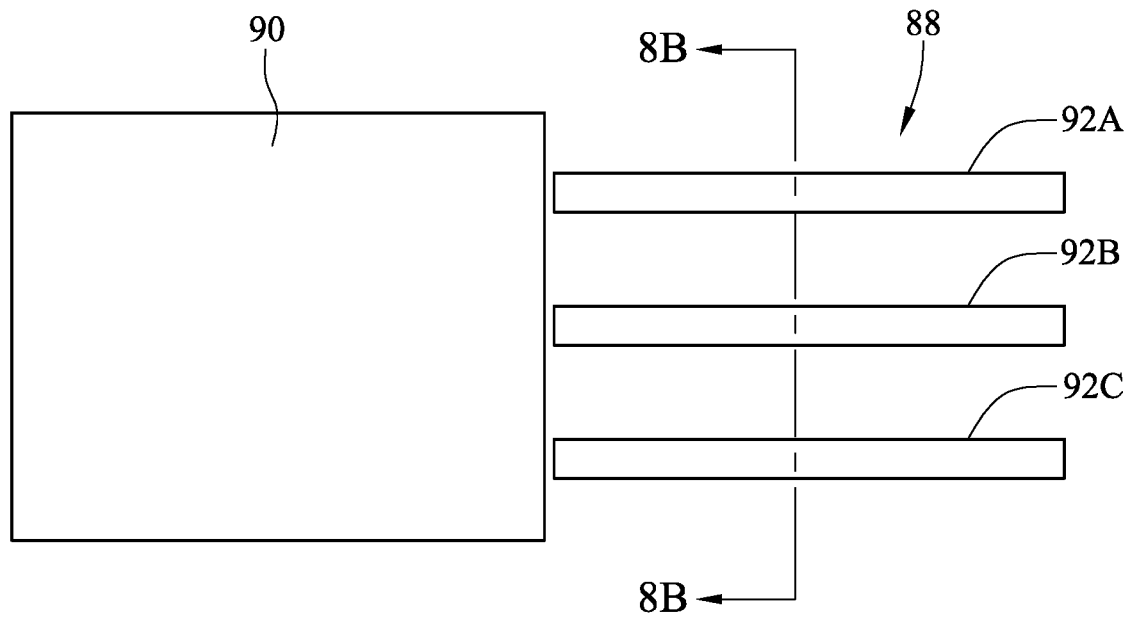
FIGS. 8A and 8B are radial and axial cross-sectional views, respectively, of a fourth embodiment of a field concentrating antenna and for a magnetic position sensor in which the antenna comprises a plurality of elongated strips positioned adjacent the position sensor.
Figure 8B:
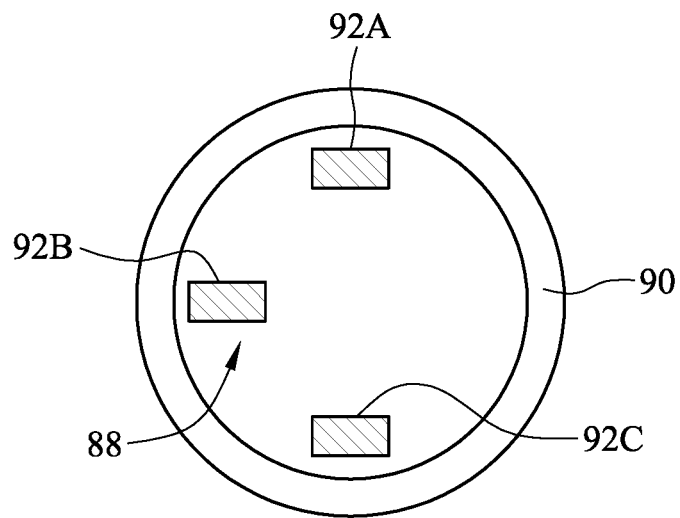

FIGS. 8A and 8B are radial and axial cross-sectional views, respectively, of a field concentrating antenna 88 and a magnetic position sensor 90. In the depicted embodiment, antenna 88 comprises a plurality of elongated strips 92A-92C positioned adjacent to position sensor 90. As discussed above, it is desirable for field concentrating antennas of the present disclosure to have long, skinny shapes such that they have a small D/L ratio. Although elongated strips 92A-92C are not round, they are thin relative to their axial length. The specific cross-sectional shape of strips 92A-92C can be different in various embodiments, and can have different thicknesses. For example, strips 92A-92C may comprise segments of thin films, sheets, or ribbons. Elongated strips 92A-92C are shown being disposed in a triangular pattern at twelve o'clock, nine o'clock, and six o'clock positions with respect to FIG. 8B. However, elongated strips 92A-92C may be positioned anywhere adjacent position sensor 90 so as to have a positive effect on the magnetic field interface with position sensor 90 as described herein. Elongate strips 92A-92C, and any of the magnetic field enhancing antennas described herein, may be held in place within the medical device using any suitable means, such as adhesive.

In the embodiment of FIGS. 8A and 8B, a plurality of small thickness-to-length ratio antennas are provided outside of the interior of position sensor 90. As such, the effect of a plurality of small mass antennas can have a cumulative effect in increasing the interface of the position sensor 90 with a magnetic field. Elongated strips 92A-92C further improve the design options for position sensor 90 by allowing field concentrating antennas to be located within any available space within the medical device that is in close proximity to the position sensor. Thus, other components, such as irrigation tubes, lead wires, guide wires, etc. can be positioned without interference from a core, and the field concentrating antennas can be fitted in space where it is available.

Figure 9:
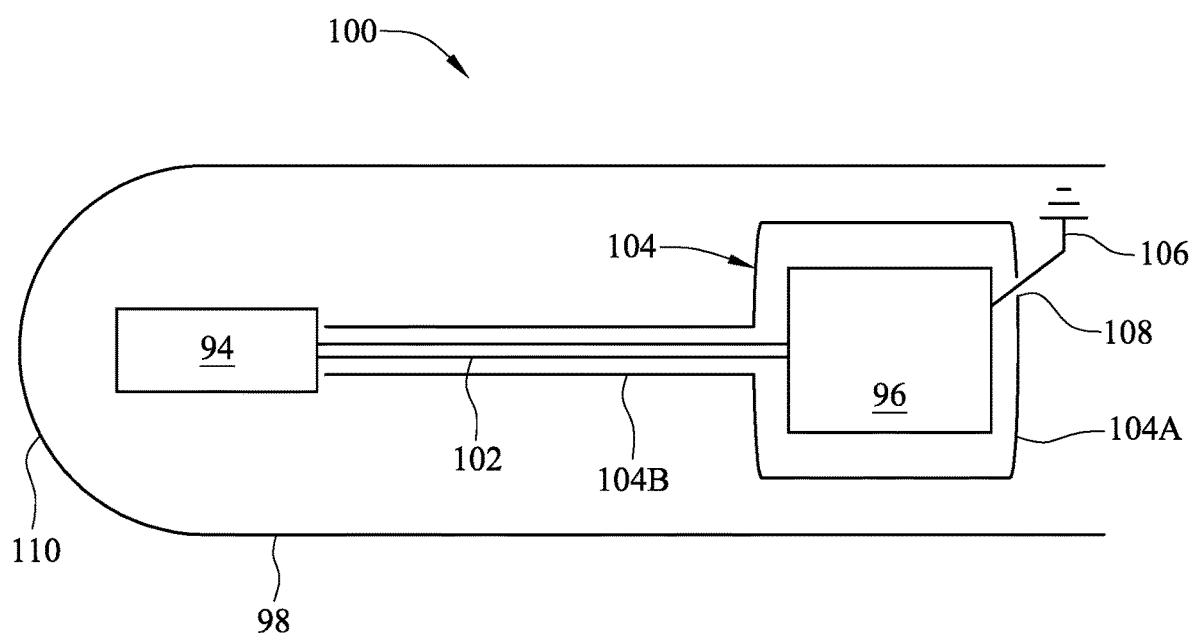
FIG. 9 is a cross-sectional view of a fifth embodiment of a field concentrating antenna for a magnetic position sensor in which the antenna is located remotely from the position sensor.

In yet another embodiment, the location of position sensor 26 could be moved away from the location for which it is configured to provide location data by remotely tethering antenna 40 to position sensor 26, as shown in FIG. 9.

FIG. 9 is a cross-sectional view of field concentrating antenna 94 for magnetic position sensor 96 in which antenna 94 is located remotely from position sensor 96 within sheath 98 of catheter 100. In the embodiment of FIG. 9, field concentrating antenna 94 is remotely tethered to position sensor 96 via conductor 102. Position sensor 96 and conductor 102 are disposed within shield 104. Position sensor 96 is grounded via wire 106, which passes through opening 108 in shield 104. Sheath 98 and catheter 100 are similar to sheath 42 and catheter 12 of FIG. 2. Likewise, position sensor 96 may be constructed similarly to position sensor 26, or any conventional magnetic position sensor.

Antenna 94 is positioned within catheter 100 at a location where it is desirable to accurately know the location. As depicted antenna 94 is positioned close to tip 110, but may be positioned close to other elements, such as diagnostic electrodes, ablation electrodes, or any other operational element. Conventionally, a position sensor provides feedback based on where it interacts with the magnetic field in which it is placed. Thus, it is conventionally desirable to locate the position sensor close to the operational element for which it is desirable to know the exact location. For example, it is desirable to know the exact location of the operational element on display screen 16 (shown in FIG. 1) relative to a model or image of the anatomy where the procedure is to be performed.

In the embodiment of FIG. 9, position sensor 96 can be placed within sheath 98 at any location where space is available without regard to the specific location within catheter 100. Antenna 94 is placed where it is desirable to know the location in the medical positioning system. Antenna 94 interacts with the magnetic field at that location, thereby generating a pseudo position signal that is relayed to position sensor 96 by conductor 102 for generation of an actual signal that can be passed to system 10 (shown in FIG. 1). Conductor 102 may be fabricated from any suitable high permeability material, such as a Metglas or nearly pure iron. Shield 104 functions to reduce magnetic noise in position sensor 96, and thus may be fabricated from a high permeability material to draw magnetic field lines away from direct engagement with position sensor 96. Shield 104 may have a variety of shapes. In the depicted embodiment, shield 104 includes sensor portion 104A that is shaped similarly to position sensor 96, and conductor portion 104B that is shaped similarly to conductor 102. Thus, shield 104 is positioned closely to the elements to be shielded to minimize consumption of space within catheter 100. However, shield 104 may have a simpler, cylindrical design to facilitate easier fabrication, but that occupies more space. As noted, shield 104 is also provided with ground wire 106. Alternatively, ground 106 may be omitted and opening 108 may be provided. Ground 106 and opening 108 may be provide to allow outside communication with position sensor 96, among other reasons.

Figure 10:
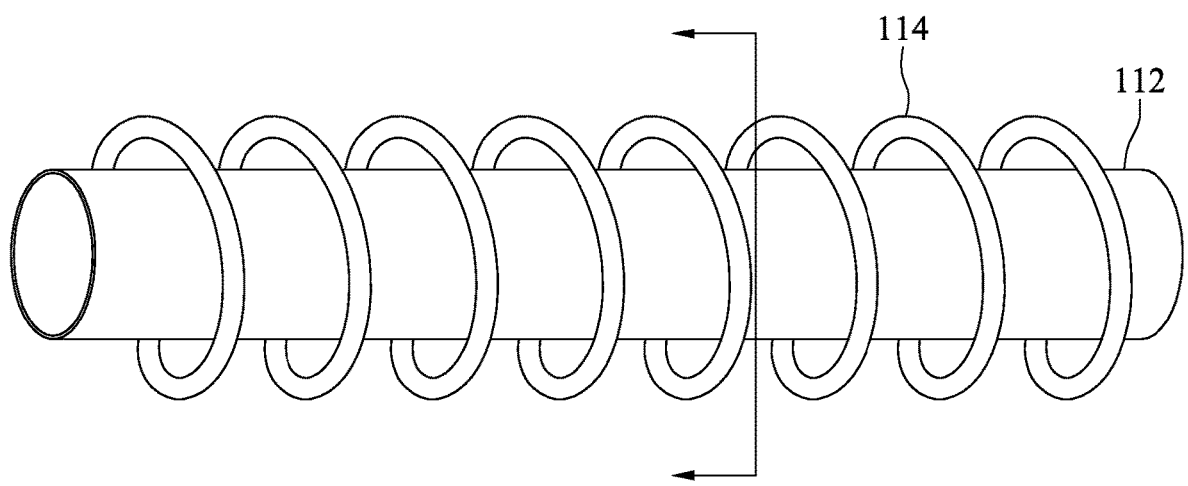
FIG. 10 is a schematic representation of a core with a coil winding on it similar to what is shown in FIG. 4.

FIG. 10 schematically depicts a typical core (e.g., a Mu metal core) of a position sensor 112 with wire windings 114 around the core of a position sensor. In this figure, the wire windings 114 are represented schematically and, in reality, they would likely be densely packed on the core of the position sensor 112.

Figure 11:
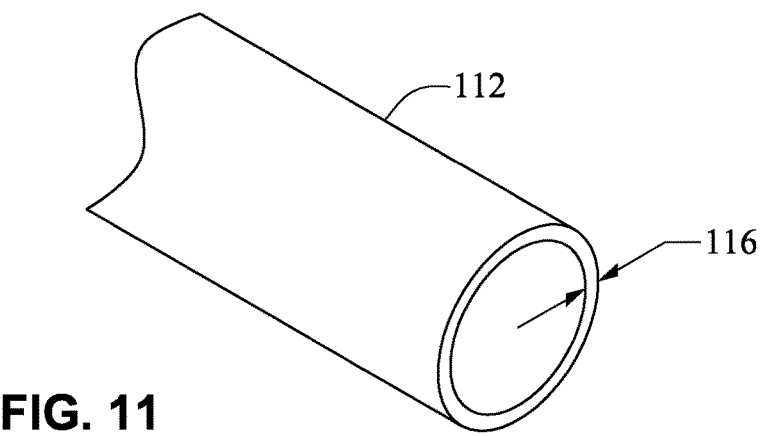
FIG. 11 is a fragmentary, isometric view of the core depicted in FIG. 10 (e.g., a Mu metal core).

FIG. 11 is a fragmentary, isometric view of the core of the position sensor 112 of FIG. 10 removed from the wire windings 114. In order to enhance the signal output from the magnetic position sensor, the core 112 may be constructed from a high permeability material. In this particular figure, the core of the position sensor 112 is represented as being constructed from Mu metal having a thickness 116 of 0.003". Cores of this sample thickness may, however, create space issues in modern catheters because of the number of components contained within the catheter body (see, for example, FIGS. 2 and 5).

Figure 12:
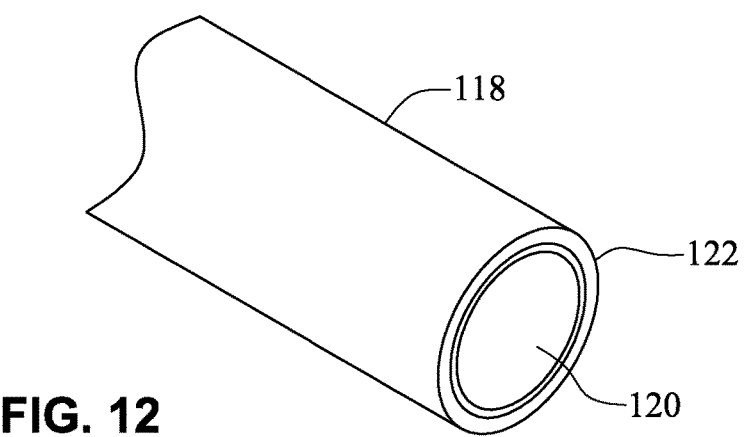
FIG. 12 is a fragmentary, isometric view of an alternative core composed of an inner cylindrical member constructed from a polymer (e.g., polyimide) and an outer cylindrical member constructed from a high permeability material (e.g., Metglas).

FIG. 12 is a fragmentary, isometric view of an alternative core 118 for a magnetic position sensor according to the present disclosure. This core 118 comprises a cylindrical polymer tube 120 (for example, a 0.0002" thick polyimide tube) surrounded by a cylinder 122 constructed from Metglas. Since the Metglas sheet that would be shaped into the Metglas cylinder 122 depicted in FIG. 12 may be extremely thin, for example, 15-75 microns thick (i.e., approximately 0.00059"-0.00295" thick), the resulting core 118 would save valuable real estate inside the catheter, freeing up space for other components. Although not shown in the figures, the Metglas on the outside of the polyimide tube may also have a C-shaped cross-section rather than being a complete annular shape. This configuration having a C-shaped cross section may be advantageous over a full cylindrical configuration since it may allow more flex lines to actually go through the center of the core than would go through the center of the core if it were a complete cylinder.

Figure 13:
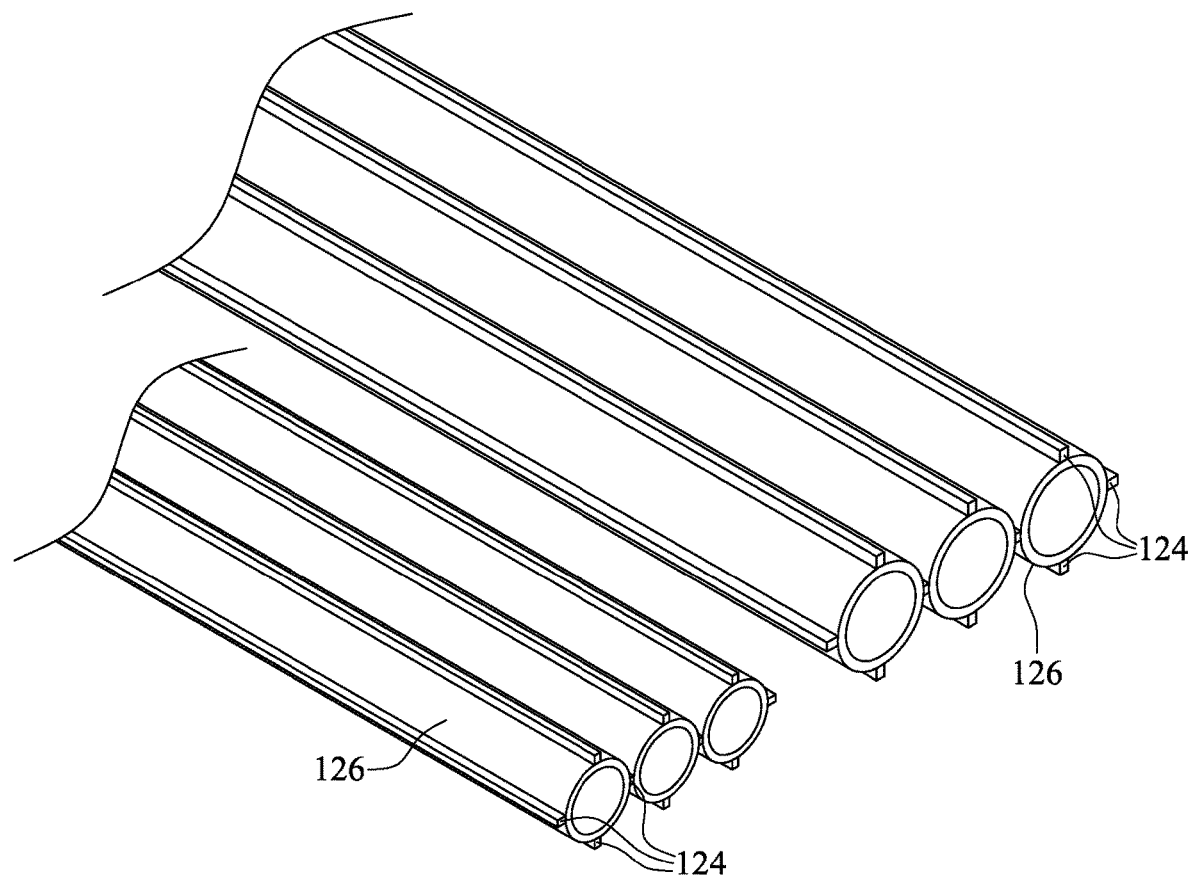
FIG. 13 is a schematic representation of a cylindrical polymer tube (e.g., a polyimide tube) having a plurality of strips constructed from high permeability material (e.g., Metglas) mounted on its exterior surface.

FIG. 13 schematically represents an alternative configuration where Metglas ribbons 124 are attached to the outer surface of a polymer inner tube—for example a polyimide tube. In other embodiments, the ribbons 124 could also be strips or wires. Although these Metglas ribbons 124 appear to be rectangularly-shaped in this figure, they each may also have a cylindrical cross section.

Figure 14:
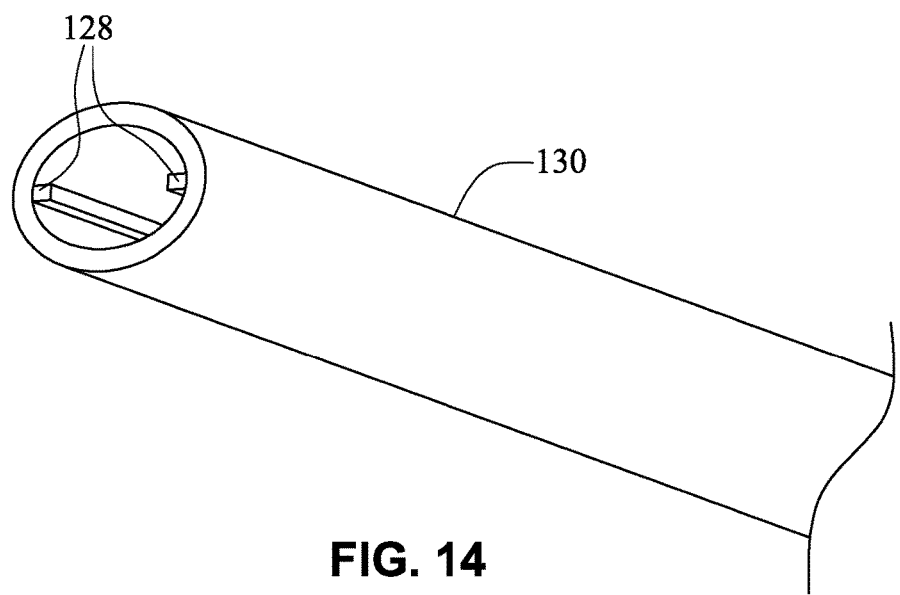
FIG. 14 is similar to FIG. 13, but schematically depicts a polymer tube (e.g., a polyimide tube) having a plurality of strips constructed from high permeability material (e.g., Metglas) mounted on its interior surface.

FIG. 14 is similar to FIG. 13, but schematically depicts Metglas ribbons 128 or strips or wires mounted to an inner surface of the polymer tube 130 (for example, a polyimide tube).

Figure 15:
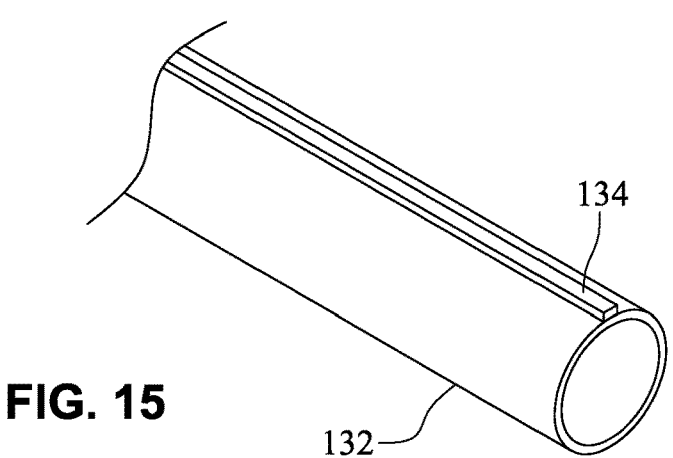
FIG. 15 is similar to FIG. 13, and is a fragmentary, isometric view that schematically depicts a Metglas ribbon or strip mounted on the exterior surface of a polyimide tube.
Figure 16A:
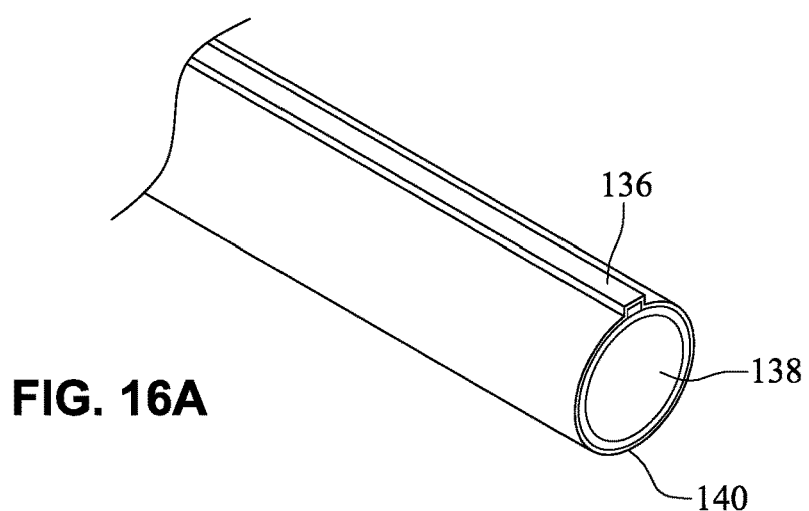
FIG. 16A schematically depicts the embodiment of FIG. 15 at a later stage of manufacture, wherein the Metglas ribbon has been mounted to the polyimide tube by a heat shrink casing.
Figure 16B:
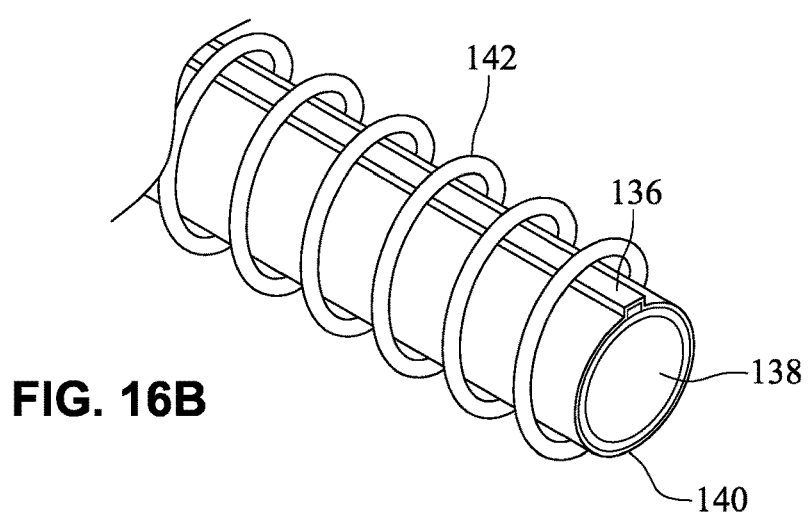
FIG. 16B schematically depicts the embodiment of 16A with a wire winding wrapped around the polyimide tube and Metglas strip
Figure 17:
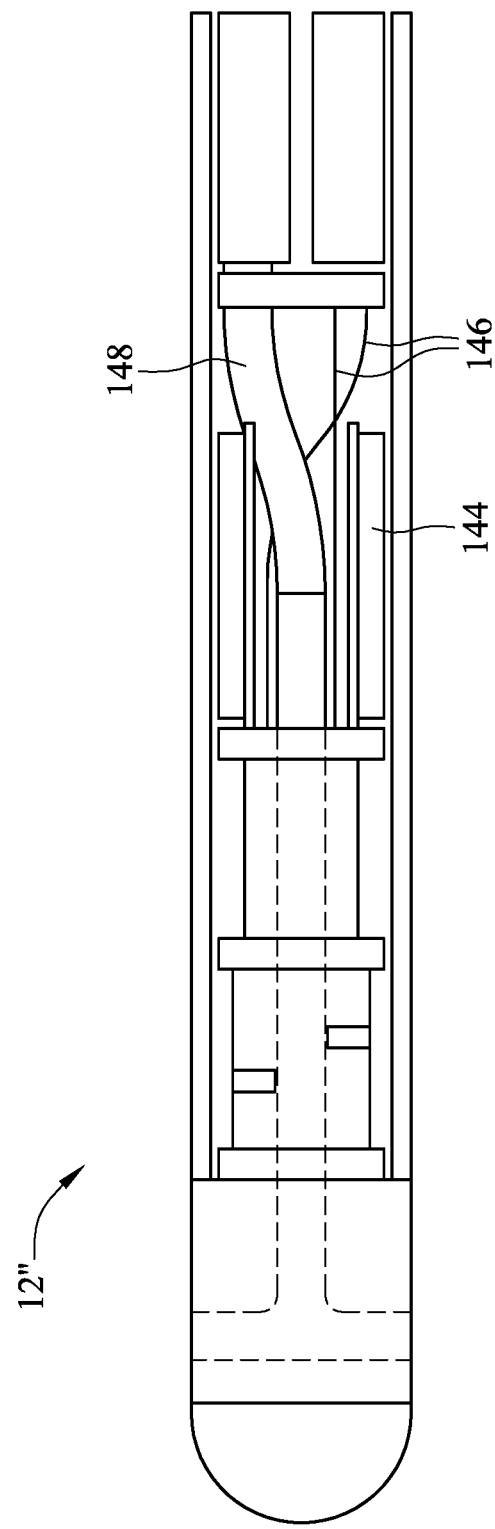
FIG. 17 is a representative irrigated catheter that includes a core and winding similar to that shown in FIG. 16B.
Figure 18:
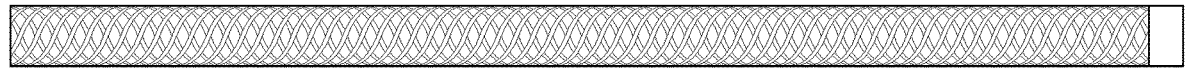
FIG. 18 depicts braided strips of high permeability material (e.g., braided Metglas strips) mounted on the exterior of a polymer tube (e.g., a polyimide tube).
Figure 19:
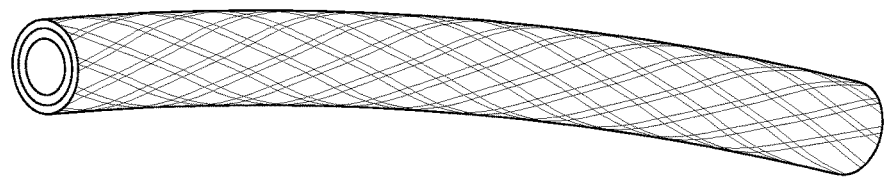
FIGS. 19-22 show various sample braid patterns for the high permeability material depicted in, for example, FIG. 18 separated from the polymer tube.

Referring next to FIGS. 15-17, an alternative construction for a magnetic position sensor according to the present disclosure is described next. FIG. 15 schematically depicts a fragmentary, isometric view of a polyimide tube 132 and a Metglas ribbon 134 attached to an outer surface of the polyimide tube 132. The Metglas ribbon could be, for example, glued in placed or wrapped with heat shrink material to hold the strip in place on the outer surface of the polyimide tube.

Referring again to FIG. 15, a plurality of high permeability ribbons or strips could be added around the entire outer perimeter of the polymer tube depicted in FIGS. 15 and 16. For example, these Metglas ribbons/strips could create a single 'picket fence' configuration surrounding the entire exterior of the polyimide tube. The plurality of Metglas strips placed adjacent to each other, potentially with their longitudinal edges in contact, could magnetically mimic the cylindrical Metglas configurations depicted in, for example, FIG. 12.

FIGS. 16A and 16B includes two embodiments similar to what is shown in FIG. 15. In FIG. 16A, a strip 136 of high permeability material (for example, a Metglas strip) is shown arranged longitudinally on an outer surface of a polymer tube 138 (for example, a polyimide tube). In this particular embodiment, a heat shrink casing 140 or sleeve holds the Metglas strip 136 on the outer surface of the polyimide tube 138. As schematically represented in FIG. 16B, a wire 142 would be wound around the outside of the assembled tube and strip assembly of FIG. 16A to complete the construction of the magnetic position sensor.

FIG. 17 schematically depicts a configuration of an irrigated catheter 12" employing the magnetic position sensor described above in connection with FIGS. 15 and 16. As shown in this figure, the magnetic position sensor 144 is mounted around fiber optic lines 146 and a fluid lumen 148 that are arranged to deliver signals and fluid, respectively, to the distal end of the catheter 12".

FIGS. 18-22 depict various embodiments of braided high permeability material (for example, braided Metglas strips). These different braid configurations could be used as an alternative to, or in combination with, the longitudinally-extending strips of high permeability material depicted in, for example, FIGS. and 16. Also, the braid could extend along portions of the catheter shaft (or along the entire catheter shaft) to magnetically shield the internal components of the catheter.

Figure 20:
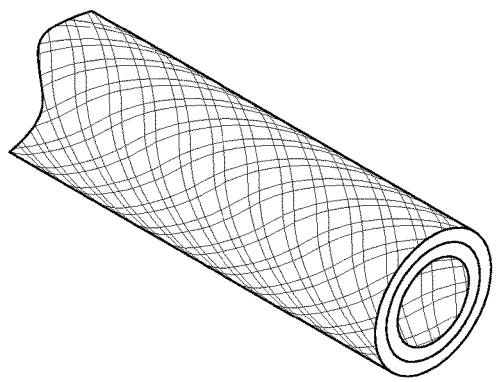
Figure 21:
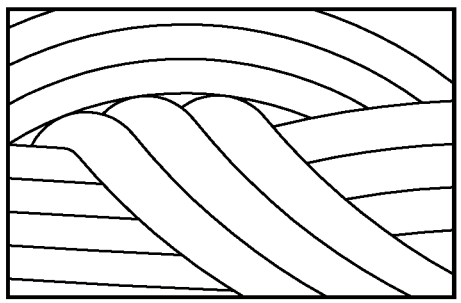
Figure 22:
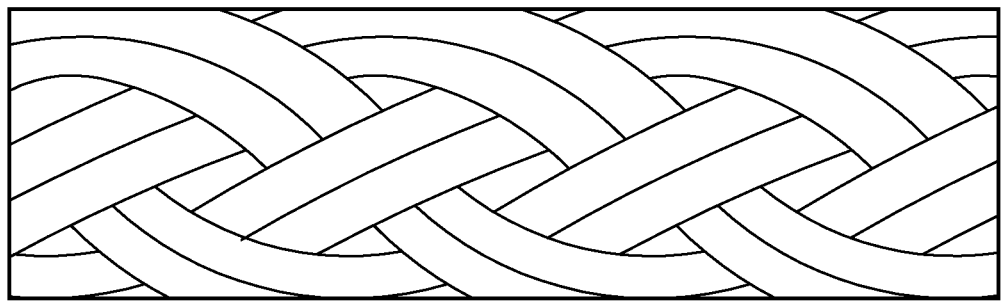

Referring to most particularly to FIG. 20, a plurality of loosely-wound strips of high permeability material (for example, Metglas strips or ribbons) are shown. The density of these strips (weave density) is adjustable depending upon parameters such as the flexibility of the material comprising the strips and the desired signal boosting function.

Figure 23:
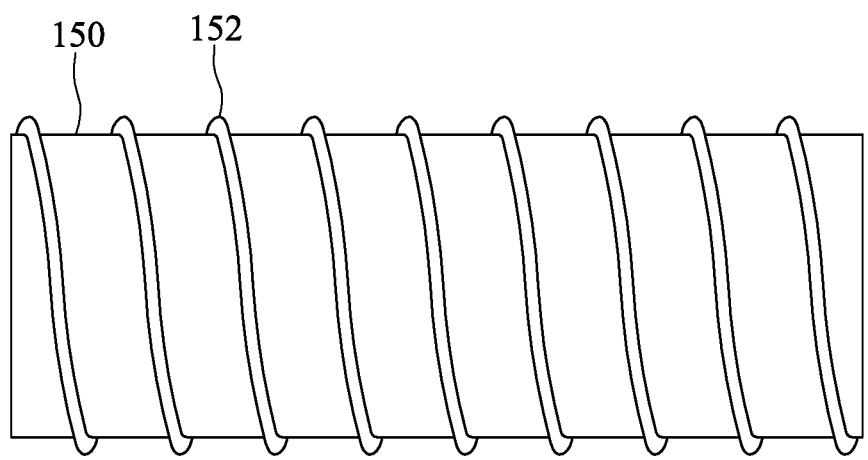
FIG. 23 depicts a helical coil of high permeability material (e.g., a Metglas ribbon) wrapped on the outer surface of a polymer tube (e.g., a polyimide tube).

FIG. 23 is a fragmentary, schematic representation of an alternative configuration wherein a polymer tube 150 (for example, a polyimide tube) has a helical coil 152 of high permeability material (for example, Metglas) wound around its exterior surface. Similar to what was described above in connection with FIG. 20, the pitch of this helical coil could be adjusted depending upon the characteristics of the high permeability material comprising the coil and the desired signal boosting impact of the resulting magnetic position sensor. Also, although FIG. 23 shows the helical coil encircling the polymer tube multiple times, it is possible that, in some embodiments, the helical coil may not fully loop around or encircle the tube even one time.

Figure 24:
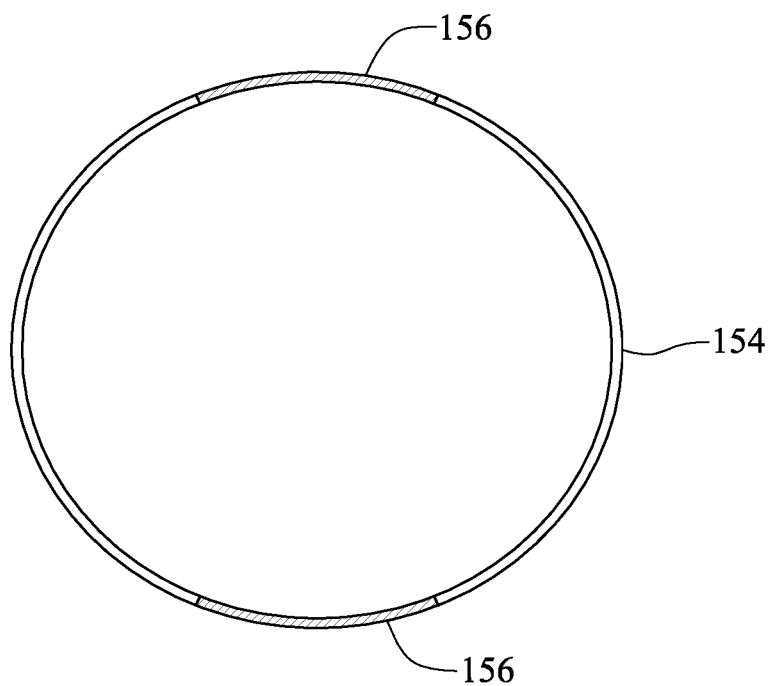
FIG. 24 is a cross-sectional view of an alternative, composite core for a magnetic position sensor, wherein two arcuate strips of the core comprise high permeability material (e.g., Metglas) and wherein the adjacent arcuate strips of the core comprise a polymer material (e.g., polyimide).

In another manufacturing option, rather than adding high permeability material to an exterior or interior surface of a polymer tube, the high permeability material could comprise part of a composite core, including, possibly, an extruded composite core. For example, FIG. 24 depicts a composite core 154 wherein arcuate Metglas strips 156 are present at the 12 o'clock position and at the 6 o'clock position in the circular cross section of this magnetic position sensor core. Those two Metglas strips 156 are separated by arcuate sections of polymer material (for example, polyimide material). Thus, in this configuration, arcuate strips of Metglas are positioned adjacent to arcuate sections of polyimide to create a core around which wire would be wound to form a magnetic position sensor. The high permeability material (Metglas in the embodiment depicted) is directly integrated into the sidewall of the core 154 during the tube-formation process. As depicted in FIG. 24, this could result in, for example, the core 154 having a sidewall thickness of approximately 0.001", if desired.

Figure 25:
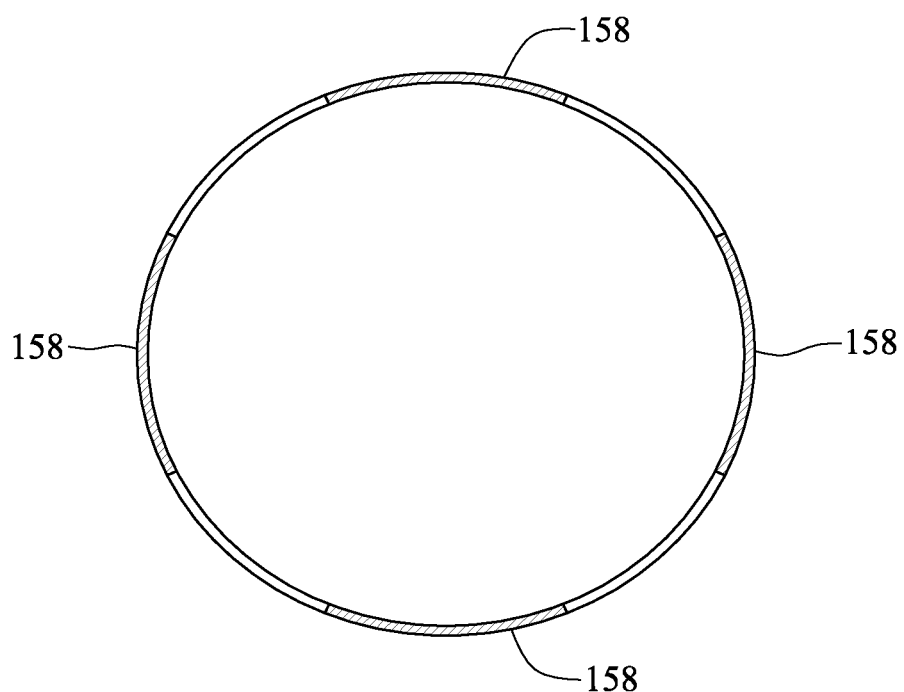
FIG. 25 is a cross-sectional view similar to what is shown in FIG. 24, but depicts a composite core comprising four arcuate strips of a high permeability material (e.g., Metglas) mounted between four arcuate strips of a polymer material (e.g., polyimide).

FIG. 25 is similar to FIG. 24, but depicts a configuration having four arcuate strips 158 of Metglas extending between four adjacent arcuate strips of polyimide. In particular, in this configuration there is a Metglas strip shown at the 12 o'clock position, the 3 o'clock position, the 6 o'clock, and the 9 o'clock position.

Figure 26:
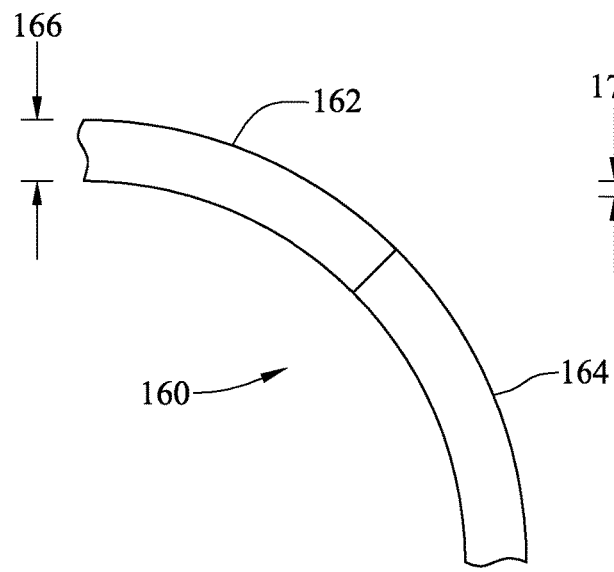
FIG. 26 depicts an enlarged, fragmentary section of a core wall comprising a Metglas segment adjacent to a polyimide segment.
Figure 27:
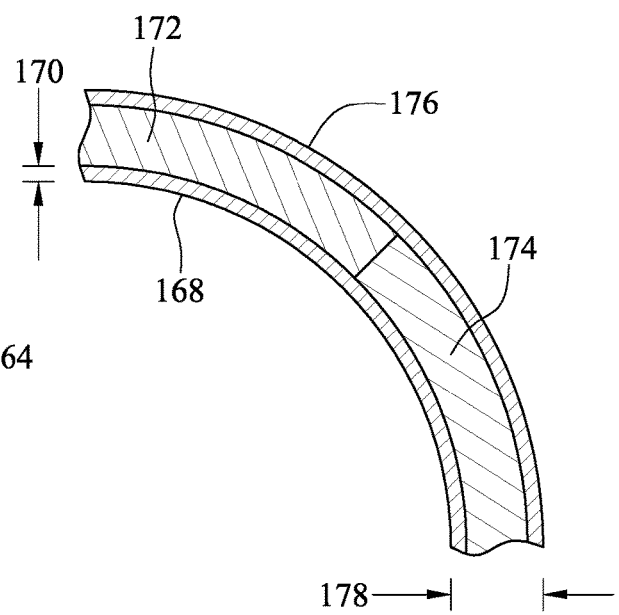
FIG. 27 is similar to FIG. 26, but depicts an embodiment wherein the adjacent Metglas and polyimide sections are encapsulated by an inner wall of polyimide and an outer wall of polyimide.

FIGS. 26-29 are fragmentary views of a section of core sidewall. For example, FIG. 26 is a fragmentary view of a section of sidewall 160 represented by the embodiments depicted in FIGS. 24 and 25. As shown in FIG. 26, the arcuate Metglas strips 162 are placed adjacent to (and are abutting in this particular configuration) polyimide strips 164. This again may permit the construction of a core having a wall thickness 166 of, for example, approximately 0.001". FIG. 27 depicts an alternative core wall construction. In this construction, a polyimide tube 168 having a thickness 170 of approximately 0.0002" comprises a cylindrical inner member. Arcuate Metglas strips 172 and arcuate polyimide strips 174 similar to those shown in FIGS. 24 and 25 are then mounted on an outer surface of the inner polyimide tube. Finally, an outer polyimide tube 176 is mounted over the Metglas strips 172 and polyimide strips 174 mounted on the outer surface of the inner polyimide tube 168. This results in a sandwiched construction, wherein the arcuate Metglas strips 172 are abutting arcuate polyimide strips 174 and all strips are sandwiched between the inner polyimide tube 168 and the outer polyimide tube 176. If the polyimide tubes are, for example, approximately 0.0002" thick and the arcuate Metglas strips 172 and the arcuate polyimide strips 174 are held to a thickness of approximately 0.0006", then the resulting core for the magnetic position sensor again may have a sidewall thickness 178 of approximately 0.001".

Figure 28:
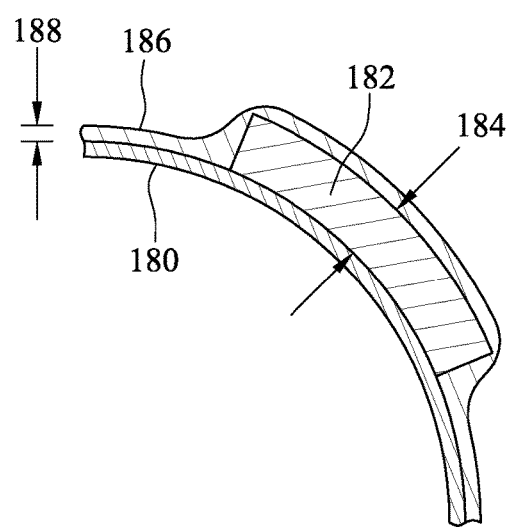
FIG. 28 depicts an embodiment similar to what is shown in FIG. 15 with a polyimide core having a Metglas strip attached to its outer surface that also includes an outer layer of polyimide to encapsulate the Metglas and hold it in place on the outer surface of the inner polyimide tube.

FIG. 28 depicts another alternative construction for the core for the magnetic position sensor. This configuration starts with a cylindrical polyimide inner member 180, represented in FIG. 8 as having a wall thickness of approximately 0.0002". A Metglas strip 182 having, for example, a thickness 184 of 0.0006" is then mounted to the outer surface of the inner polymer tube, similar to what is shown in, for example, FIG. 15. Next, a polyimide layer 186 with a thickness 188 of, for example, approximately 0.0008" is then overlaid on the outer surface of the inner polyimide tube 180 and Metglas strip 182 (or strips) as shown. This results in a core for the magnetic position sensor having sections that are approximately 0.001" thick and sections with a wall thickness of approximately 0.0016". The coil windings would be then wound on the outer surface of this assembly as shown in, for example, FIGS. 4, 10, and 16.

Figure 29:
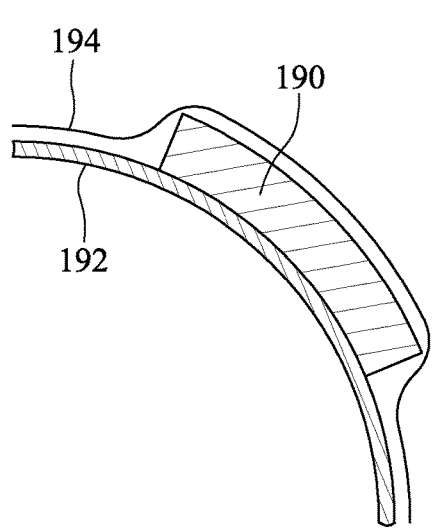
FIG. 29 depicts a possible intermediate step where a thermal plastic strip stabilizer may be used to keep the Metglas strip in position on the outer surface of the inner polyimide tube during construction of, for example, a composite core such as the one depicted in FIG. 27 or FIG. 28.

FIG. 29 depicts a potential intermediate step during the construction of a core for a magnetic position sensor. In this embodiment, a Metglas strip 190 is again added to (e.g., adhered to) an outer surface of a cylindrical polyimide tube 192. In this embodiment, however, a thin thermal plastic strip stabilizer 194 has been placed over the Metglas strip 190 to stabilize the strip 190 on the outer surface of the polyimide tube 192. This thermal plastic strip stabilizer 194 may remain in place during the remaining construction of the core for the magnetic position sensor. In particular, another layer (e.g., of polyamide) could be added over the thermal plastic strip, similar to the outer polyimide layer depicted in FIG. 28, or, alternatively, the coil wire could be wound directly on the outer surface of the polyimide tube with the Metglas ribbons held in place by the thermal plastic strip stabilizer.

Figure 30:
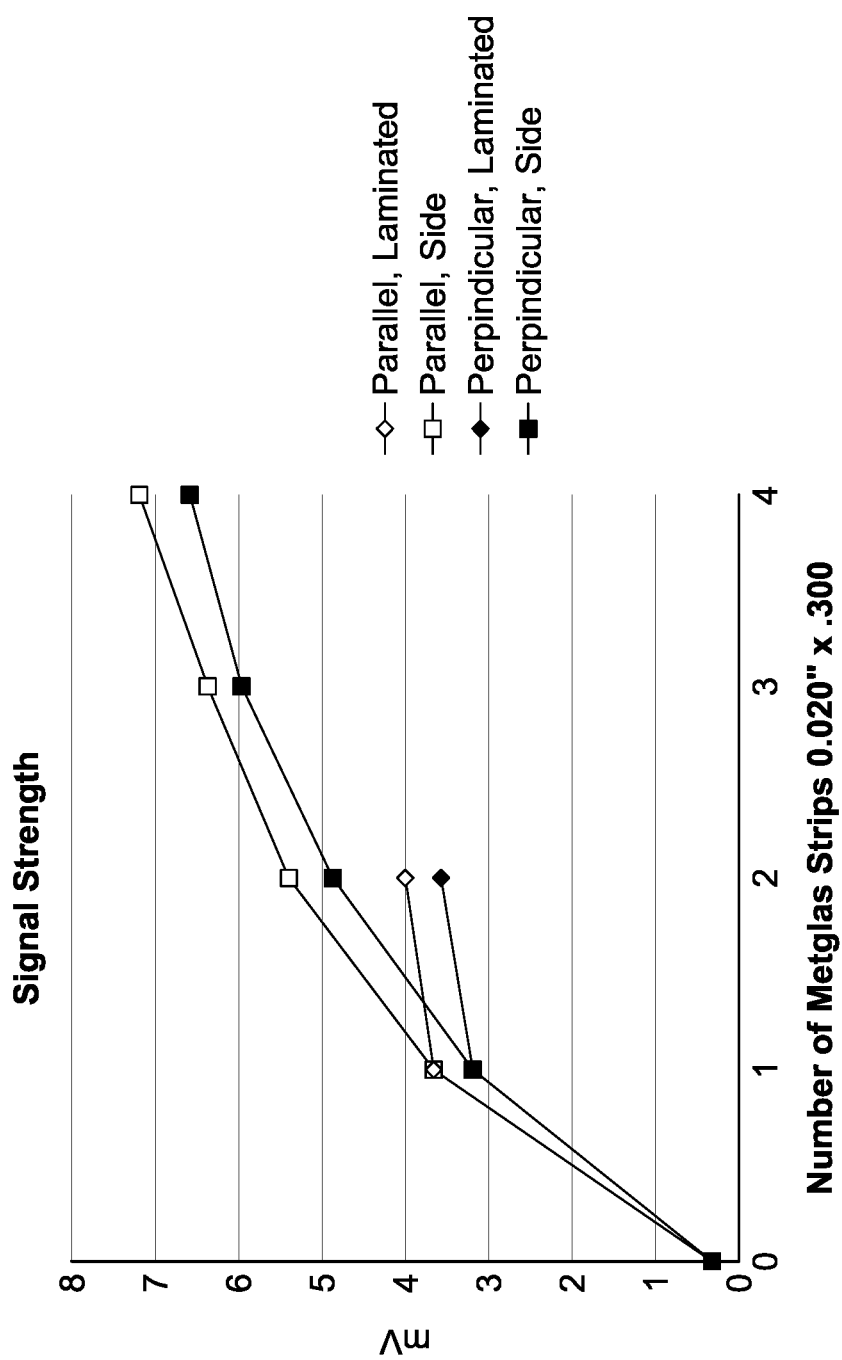
FIG. 30 depicts how signal strength from a magnetic position sensor constructed according to the disclosed embodiments may vary depending upon how the strips of, for example, Metglas are cut from a larger sheet and whether those Metglas strips are laminated or placed adjacent to each other.
Figure 31:
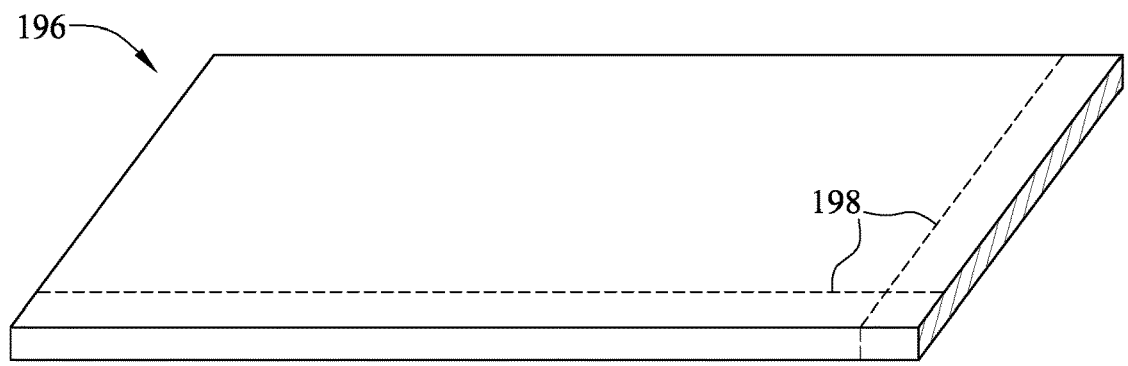
FIG. 31 schematically depicts a sheet of Metglas material and possible cut lines (shown as dashed lines) for creating Metglas strips/ribbons for use in the various embodiments disclosed herein.

FIG. 30 depicts the results of an experiment to measure signal strength output by a magnetic position sensor while varying various parameters. In this experiment, strips of Metglas were placed in a open "universal" coil (i.e., a coil without a core) so that different cores could be placed inside the coil while measuring the resulting voltage. While Metglas is an amorphous alloy, there is a preferred orientation of the material in relation to the orientation of the magnetic flux. This is represented schematically in FIG. 31, which depicts a sheet 196 of Metglas material having a preferred orientation relative to the orientation of magnetic flux. As represented by the dash lines 198 in FIG. 31, for some of the experiments represented by lines on the graph of FIG. 30, Metglas strips were cut perpendicular to this preferred orientation, and in other experiments represented by other lines on the graph of FIG. 30, the Metglas ribbons were cut parallel to the preferred orientation. This is represented in FIG. 30 by the words "parallel" and "perpendicular."

Figure 32:
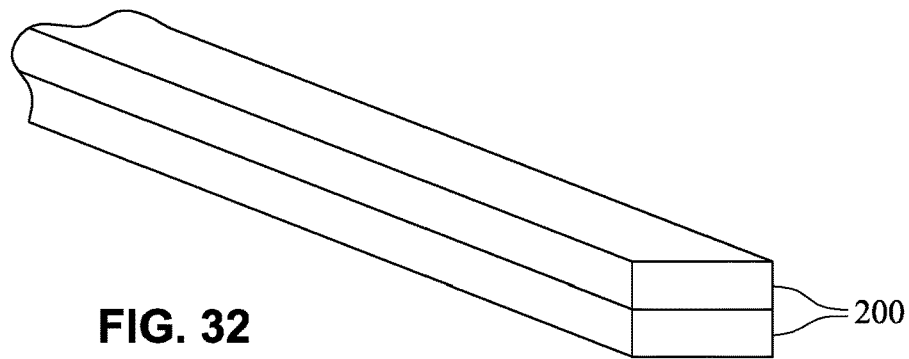
FIG. 32 depicts a "laminated" configuration of two Metglas strips as that term is referenced in FIG. 30.
Figure 33:
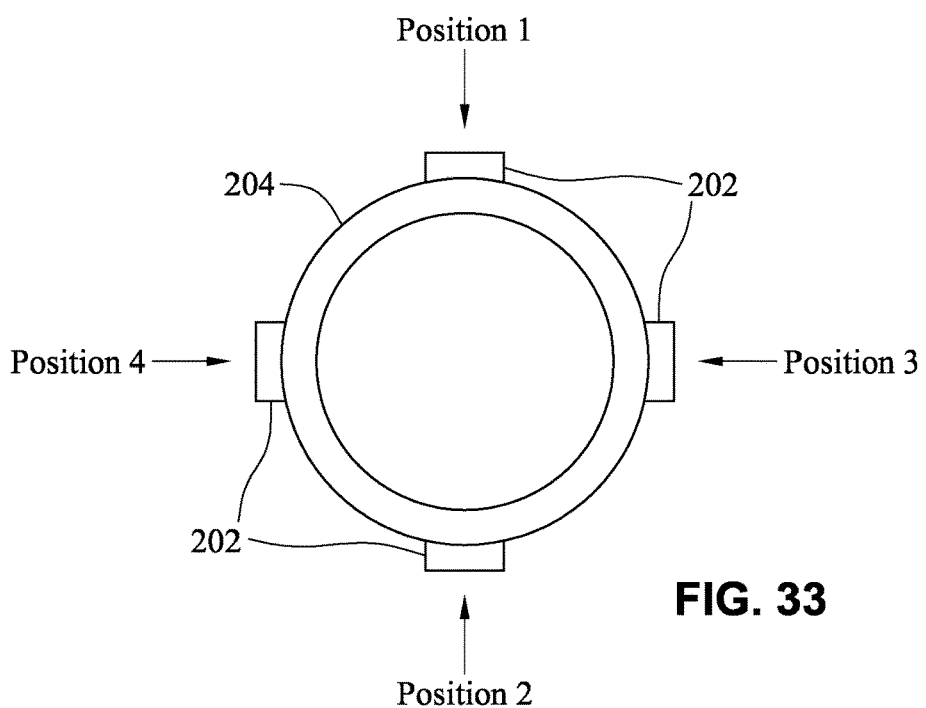
FIG. 33 depicts a "side" construction of Metglas strips as that term is used in FIG. 30.

In FIG. 30, two plot or graph lines are also labelled with the designation "laminated." This indicates that strips 200 of Metglas having a stack configuration similar to what is schematically represented in FIG. 32 war inserted in the universal coil to capture the data represented in the corresponding lines on FIG. 30. The two upper lines on FIG. 30 include the designation "side." As discussed further below, this "side" designation refers to Metglas strips 202 oriented relative to a polymer core 204 as shown schematically in FIG. 33.

Comparing the top two lines in FIG. 30, it becomes apparent that whether the Metglas strips are cut parallel to or perpendicular to the preferred orientation has someone limited influence or effect on the resulting signal strength of the magnetic position sensor. This limited effect is also apparent by similarly comparing the lower two lines (i.e., the lines that each end in a diamond in FIG. 30). Of greater effect, as also clearly represented in FIG. 30, is the placement of the Metglas strips relative to each other. Lower signal strengths were received from the magnetic position sensor when the two Metglas strips were laminated (i.e., when they had the configuration depicted in schematically in FIG. 32).

Looking now more closely at the upper two lines in FIG. 30, which carry the designation "side," further details of the experiment are described next. When one Metglas strip was used it was placed at "position 1" shown in FIG. 33. When two Metglas strips were used, they were placed at position 1 and position 2, respectively (see FIG. 33). When three Metglas strips were used, they were placed at positions 1, 2, and 3, shown in FIG. 33. Finally, when four Metglas strips were used in the experiment, they were placed a positions 1-4 shown in FIG. 33.

Figure 34:
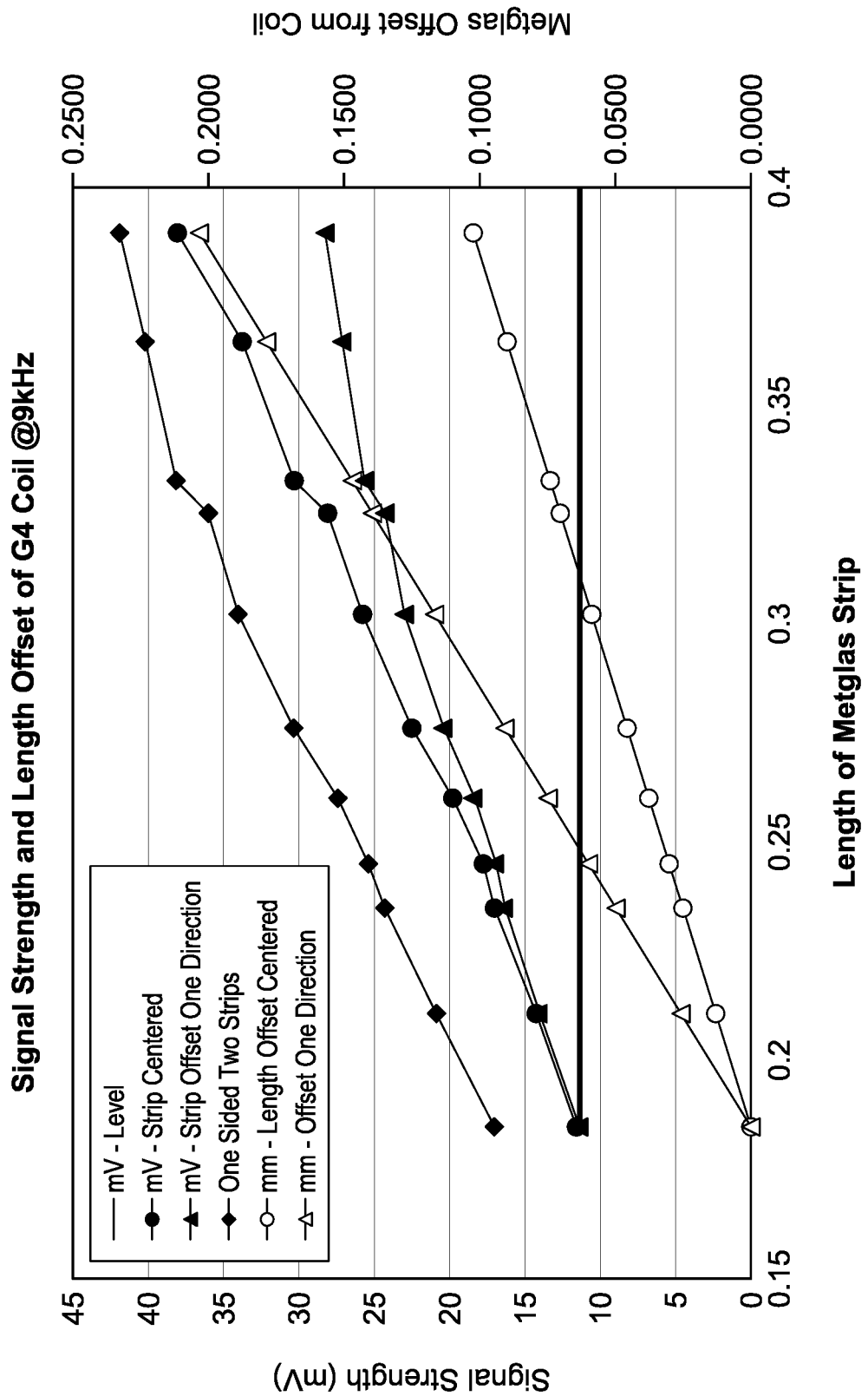
FIG. 34 includes some lines representing signal strength as a function of Metglas strip length (also taking into account two different strip positions relative to the wire coil position), and other lines representing Metglas strip offset from a coil end or the coil ends versus strip length (also taking into account two different strip positions relative to the wire coil position).

FIG. 34 includes, the following six lines:
1. mV—level: a horizontal line showing the lowest level (threshold for) voltage which must be met in order for a sensor to be deemed adequate for one particular system. It is a reference line on the graph to give meaning to the rest of the data.
2. mV—strip centered: the voltage response of the coil when a strip of length associated with the X-axis is placed inside the coil, but centered in the coil such that a little bit of the strip extends beyond both distal and proximal edges of the coil.
3. mm—length offset centered: The same strip as the previous bullet point, this merely shows the length of the strip (in mm) that would extend beyond the coil itself. This number has manufacturability implications.
4. mV—strip offset one direction: Voltage response when taking a strip of length associated with the X-axis, and placing it so that it is flush on one side of the coil (distal) and only extends one direction from the coil on the proximal side.
5. mm—offset one direction: physical offset when doing the experiment from the bullet directly above.
6. One sided two strips: Until this bullet, all the data is only with a single strip of Metglas 0.020" wide. This line is an estimation of what the voltage response would be if there were two strips inside the coil instead of one. Also, this Metglas strip would be assumed to be sticking out only one side like the two lines labeled "offset one direction."

Thus, line #1 (referring to the item number above) is a substantially horizontal line near the bottom of the cart representing the lowest level of sensor signal strengths that may be used effectively in a particular system for locating a magnetic position sensor. In other words, for some systems, the sensor must produce at least this voltage in order to be recognized by the medical positioning system. Next, there are two lines on the chart that reference "mm" (i.e., lines #3 and #5 in the numbered list above). To read the data associated with these two lines, you must use the horizontal scale ("Length of Metglas strip") and the right-hand vertical scale ("Metglas offset from coil"). Comparing these lines, it is apparent that, for the tested configurations, the greater the offset for a particular length of Metglas, the higher the resulting signal strength. The lower of these two lines carries the designation "mm—length of offset centered." As noted above, this line shows the length of the strip in millimeters that would extend beyond the coil itself when the Metglas strip is of the designated length (x-axis). On the other hand, the upper of these two lines (which carries the designation "mm—offset one direction") represents the physical offset of the Metglas strip when the distal end of the coil is aligning with the distal end of the Metglas strip, and the proximal end of the Metglas strip extends proximally from the proximal end of the coil. Comparing the line having the designation "mV—strip centered" to the line carrying the designation "mV—strip offset one direction," it is apparent that for a given length of Metglas strip, wherein that length is longer than the longitudinal length of the coil, if the strip is centered on the coil and thereby extends the same distance from each end of the coil, the resulting signal strength is greater than if the same length Metglas strip is mounted relative to the coil so as to extend only from one end of the coil.

Although several embodiments have been described above with a certain degree of particularity, those skilled in the art could make numerous alterations to the disclosed embodiments without departing from the spirit of the present disclosure. It is intended that all matter contained in the above description or shown in the accompanying drawings shall be interpreted as illustrative only and not limiting. Changes in detail or structure may be made without departing from the present teachings. The foregoing description and following claims are intended to cover all such modifications and variations.

Various embodiments are described herein of various apparatuses, systems, and methods. Numerous specific details are set forth to provide a thorough understanding of the overall structure, function, manufacture, and use of the embodiments as described in the specification and illustrated in the accompanying drawings. It will be understood by those skilled in the art, however, that the embodiments may be practiced without such specific details. In other instances, well-known operations, components, and elements have not been described in detail so as not to obscure the embodiments described in the specification. Those of ordinary skill in the art will understand that the embodiments described and illustrated herein are non-limiting examples; and, thus, it can be appreciated that the specific structural and functional details disclosed herein may be representative and do not necessarily limit the scope of the embodiments, the scope of which is defined solely by the appended claims.

Reference throughout the specification to "various embodiments," "some embodiments," "one embodiment," "an embodiment," or the like, means that a particular feature, structure, or characteristic described in connection with the embodiment is included in at least one embodiment. Thus, appearances of the phrases "in various embodiments," "in some embodiments," "in one embodiment," "in an embodiment," or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features structures, or characteristics of one or more other embodiments without limitation.

It will be appreciated that the terms "proximal" and "distal" may be used throughout the specification with reference to a clinician manipulating one end of an instrument used to treat a patient. The term "proximal" refers to the portion of the instrument closest to the clinician and the term "distal" refers to the portion located furthest from the clinician. It will be further appreciated that for conciseness and clarity, spatial terms such as "vertical," "horizontal," "up," and "down" may be used herein with respect to the illustrated embodiments. However, surgical instruments may be used in many orientations and positions, and these terms are not intended to be limiting and absolute.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. A medical device configured for diagnosis or treatment of organic tissue within a patient, the medical device comprising the following:
    an elongate member configured to be received within the patient, the elongate member having a lumen extending between a proximal end and a distal end; and
    a position sensor disposed within the lumen proximate the distal end of the elongate member, the position sensor including
        a coil wound to form a central passage and configured to generate a current flow when subject to a magnetic field, and
        a high-permeability antenna having at least a portion disposed outside the central passage to concentrate the magnetic field into the coil and increase the current flow.

2. The medical device of claim 1, wherein the high-permeability antenna includes a body passing through the central passage and having an axial length longer than that of the coil.

3. The medical device of claim 2, wherein the body is circumferentially curved in a direction of windings of the coil.

4. The medical device of claim 2, further including a plurality of bodies disposed adjacent the coil.

5. The medical device of claim 1, wherein the high-permeability antenna includes a first mass disposed adjacent the coil.

6. The medical device of claim 5, wherein the first mass is in contact with the coil outside of the central passage.

7. The medical device of claim 5, wherein the first mass is displaced from the coil along an axis of the coil.

8. The medical device of claim 5, further including a second mass disposed opposite the first mass relative to the coil.

9. The medical device of claim 1, wherein the antenna includes
a first mass positioned outside of the central passage from the sensor; and
a conductor electrically coupling the first mass and the coil.

10. The medical device of claim 9, further including a shield extending from the first mass to surround the conductor and the coil.

11. The medical device of claim 10, wherein the antenna further includes an opening in the shield adjacent the sensor, or a ground extending through the shield from the sensor.

12. The medical device of claim 1, wherein the antenna comprises metallic glass material.

13. The medical device of claim 1, further comprising a core disposed completely within the central passage of the coil.

14. The medical device of claim 1, wherein the high-permeability antenna has an outer diameter greater than that of the coil.

15. The medical device of claim 1, further comprising:
an inner tube extending through the coil; and
a conductor extending from the coil toward the proximal end of the elongate member.

16. The medical device of claim 1, further comprising:
an operational element disposed proximal the distal end of the elongate member; and
a handle disposed at the proximal end of the elongate member and adapted to control deflection of the distal end.

17. A position sensor assembly for a medical device, the position sensor assembly comprising:
a body defining an internal lumen;
a wire winding spirally wound around the body; and
a magnetic flux antenna offset from the wire winding along a central axis of the wire winding and within the body, wherein the magnetic flux antenna is configured and arranged to concentrate a received magnetic field into the wire winding.

18. The sensor assembly of claim 17, wherein the antenna comprises a thin strip of material, and
wherein the magnetic flux antenna is not configured and arranged to transmit a signal.

19. The sensor assembly of claim 17, wherein the antenna includes a first mass of material having a permeability greater than that of the wire winding; and
wherein the magnetic flux antenna is further configured and arranged via the increased magnetic flux sensed from the received magnetic field to facilitate decreased wire winding diameter, and/or number of coil windings, and/or allow for the use of wire windings with less desirable material characteristics while maintaining magnetic flux.

20. The sensor assembly of claim 17, further comprising a core disposed within the wire winding; and
wherein the magnetic flux antenna is further configured and arranged to increase the permeability of the core or increase the magnetic field strength impacting the core.

21. The sensor assembly of claim 17, further comprising a plurality of magnetic flux antennas disposed outside of the wire winding and within the body.

22. The sensor assembly of claim 17, further comprising:
a conductor electrically coupling the wire winding and the magnetic flux antenna; and
a shield surrounding the wire winding and the conductor.

23. A medical device comprising:
an elongate sheath defining a lumen;
a position sensor disposed within the lumen;
an electrode exposed to an exterior of the elongate sheath; and
a magnetic antenna disposed within the sheath and apart from the position sensor, wherein the magnetic antenna is configured and arranged to receive and concentrate a magnetic field into the position sensor.

24. The medical device of claim 23, wherein the position sensor comprises a coil, and wherein the magnetic antenna is not configured and arranged to transmit a signal.

25. The medical device of claim 24, wherein the coil includes a core having a permeability greater than that of air.

26. The medical device of claim 25, wherein the permeability of the magnetic antenna is greater than that of the core; and wherein the magnetic antenna is further configured and arranged to increase the permeability of the core or increase the magnetic field strength impacting the core.

27. The medical device of claim 24, wherein the magnetic antenna comprises a thin strip of material extending generally parallel to a central axis of the coil.

28. The medical device of claim 24, further including an additional magnetic antenna disposed apart from the other magnetic antenna.

29. A method of increasing the signal output of a magnetic position sensor, the method comprising:
configuring a magnetic position sensor comprising a coil to generate a current flow when subject to a magnetic field;
mounting the position sensor within a medical device; and
placing at least a portion of a high permeability antenna outside of the magnetic position sensor and within the medical device so as to be configured to receive and concentrate a magnetic field into the coil and increase the current flow within the coil.

30. The method of claim 29, wherein the high permeability antenna is positioned to funnel magnetic flux to the magnetic position sensor, and wherein the high permeability antenna is not configured and arranged to transmit a signal.

31. The method of claim 29, further comprising spacing the high permeability antenna from the magnetic position sensor along a longitudinal axis defined by a central axis of the coil.

32. The method of claim 29, further comprising shaping the high permeability antenna to be long and skinny.

33. The method of claim 29, further comprising connecting the magnetic position sensor and the high permeability antenna with a conductor.

34. The method of claim 33, further comprising shielding the magnetic position sensor and the conductor with a high permeability structure.

* * * * *